(12) United States Patent
Ozaki et al.

(10) Patent No.: US 10,405,783 B2
(45) Date of Patent: Sep. 10, 2019

(54) CONCENTRATION MEASUREMENT DEVICE AND CONCENTRATION MEASUREMENT METHOD

(71) Applicant: HAMAMATSU PHOTONICS K.K., Hamamatsu-shi, Shizuoka (JP)

(72) Inventors: Takeo Ozaki, Hamamatsu (JP); Susumu Suzuki, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 273 days.

(21) Appl. No.: 15/611,142

(22) Filed: Jun. 1, 2017

(65) Prior Publication Data

US 2017/0258381 A1 Sep. 14, 2017

Related U.S. Application Data

(62) Division of application No. 14/377,931, filed as application No. PCT/JP2012/083474 on Dec. 25, 2012, now Pat. No. 9,700,248.

(30) Foreign Application Priority Data

Feb. 20, 2012 (JP) .................................. 2012-034032

(51) Int. Cl.
*A61B 5/1455* (2006.01)
*G01N 21/31* (2006.01)
(Continued)

(52) U.S. Cl.
CPC ........ *A61B 5/14552* (2013.01); *A61B 5/1455* (2013.01); *A61B 5/6814* (2013.01);
(Continued)

(58) Field of Classification Search
CPC . A61B 5/0205; A61B 5/1455; A61B 5/14551; A61B 5/14552; A61B 5/6814
See application file for complete search history.

(56) References Cited

U.S. PATENT DOCUMENTS

| | | |
|---|---|---|
| 5,564,418 A | 10/1996 | Ozaki et al. |
| 2004/0064054 A1 | 4/2004 | Clift |

(Continued)

FOREIGN PATENT DOCUMENTS

| | | | |
|---|---|---|---|
| JP | H07-255709 A | 10/1995 | |
| JP | H09-19408 A | 1/1997 | |

(Continued)

OTHER PUBLICATIONS

Susumu Suzuki et al., "A Tissue Oxygenation Monitor using NIR Spatially Resolved Spectroscopy," Proceedings of SPIE, pp. 582-592, Jan. 1999, vol. 3597.

(Continued)

*Primary Examiner* — Eric F Winakur
*Assistant Examiner* — Chu Chuan Liu
(74) *Attorney, Agent, or Firm* — Drinker Biddle & Reath LLP

(57) ABSTRACT

A concentration measurement apparatus includes a probe, having a light incidence section making measurement light incident on the head and a light detection section detecting the measurement light that has propagated through the interior of the head, and a CPU determining temporal relative change amounts of oxygenated hemoglobin concentration and deoxygenated hemoglobin concentration and determining a correlation coefficient of the relative change amounts and a polarity of a slope of a regression line.

10 Claims, 15 Drawing Sheets

(51) Int. Cl.
*A61B 5/00* (2006.01)
*G06F 17/17* (2006.01)

(52) U.S. Cl.
CPC .......... *G01N 21/314* (2013.01); *G06F 17/17* (2013.01); *G01N 2021/3144* (2013.01)

(56) References Cited

U.S. PATENT DOCUMENTS

| | | | |
|---|---|---|---|
| 2004/0267324 A1* | 12/2004 | Geheb | A61B 5/11 607/5 |
| 2005/0080323 A1 | 4/2005 | Kato | |
| 2007/0167704 A1 | 7/2007 | Chance | |
| 2008/0146901 A1 | 6/2008 | Katura et al. | |
| 2008/0262327 A1* | 10/2008 | Kato | A61B 5/14553 600/324 |

FOREIGN PATENT DOCUMENTS

| | | |
|---|---|---|
| JP | 2004-154481 | 6/2004 |
| JP | 2008-148797 A | 7/2008 |
| JP | 2008-167818 A | 7/2008 |
| JP | 2009-125402 A | 6/2009 |
| WO | WO 92/021283 | 12/1992 |
| WO | WO 2006/006143 A1 | 1/2006 |
| WO | WO 2006/009178 | 1/2006 |

OTHER PUBLICATIONS

English-language translation of International Preliminary Report on Patentability (IPRP) dated Sep. 4, 2014 that issued in WO Patent Application No. PCT/JP2012/083474.

N. Nagdyman, "Cerebral oxygenation measured by near-infrared spectroscopy during circulatory arrest and cardiopulmonary resuscitation", British Journal of Anaesthesia, vol. 91, No. 3, Sep. 1, 2003, p. 438-p. 442, XP055208245.

G. Taga et al., "Spontaneous oscillation of oxy- and deoxy-hemoglobin changes with a phase difference throughout the occipital cortex of newborn infants observed using non-invasive optical topography", Neuroscience Letters, vol. 282, Jan. 1, 2000, p. 101-p. 104, XP002569197.

X. Cui et al., "Functional near infrared spectroscopy (NIRS) signal improvement based on negative correlation between oxygenated and deoxygenated hemoglobin dynamics", Neuroimage, Academic Press, vol. 49, No. 4, Feb. 15, 2010, p. 3039-p. 3046, XP026853125.

* cited by examiner

*Fig.2*
(a)
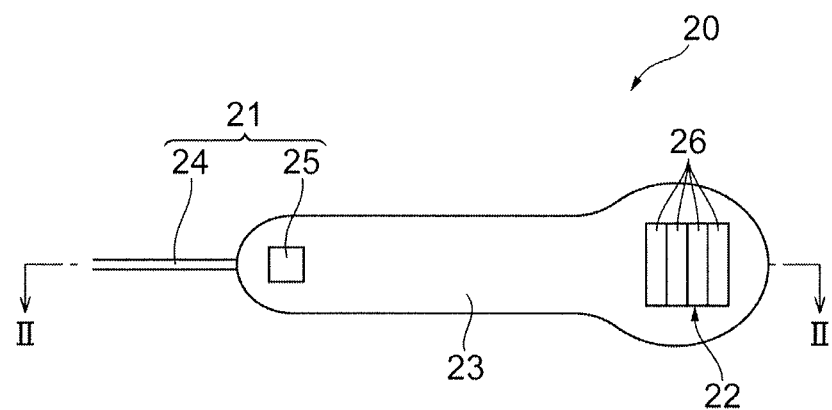
(b)
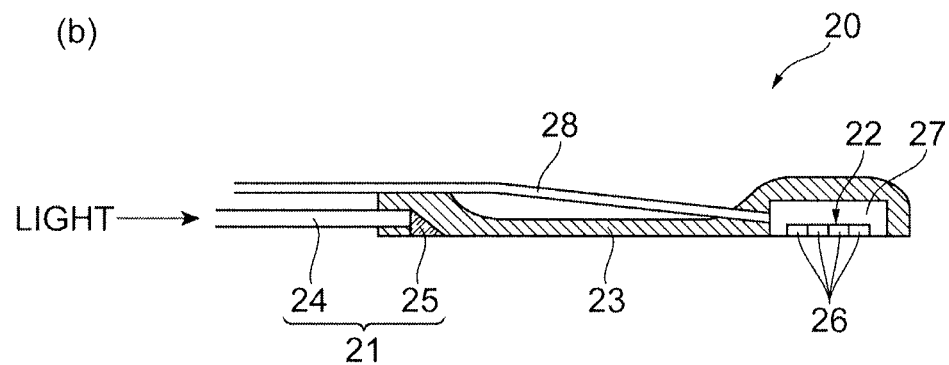

Fig.9
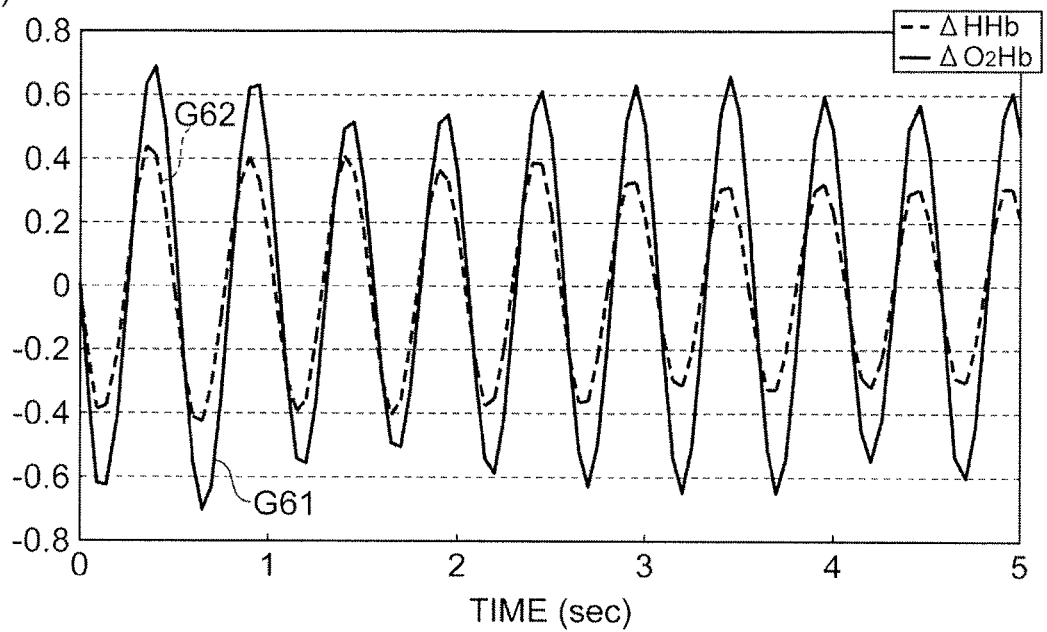
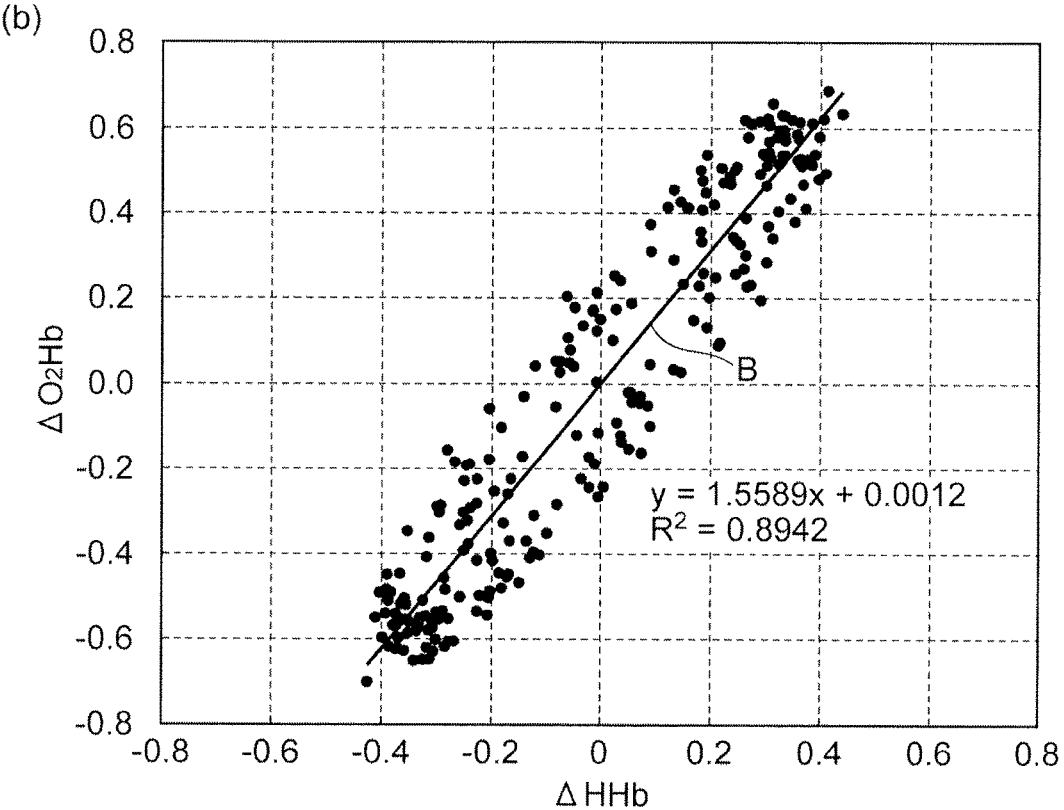

Fig.10
(a)
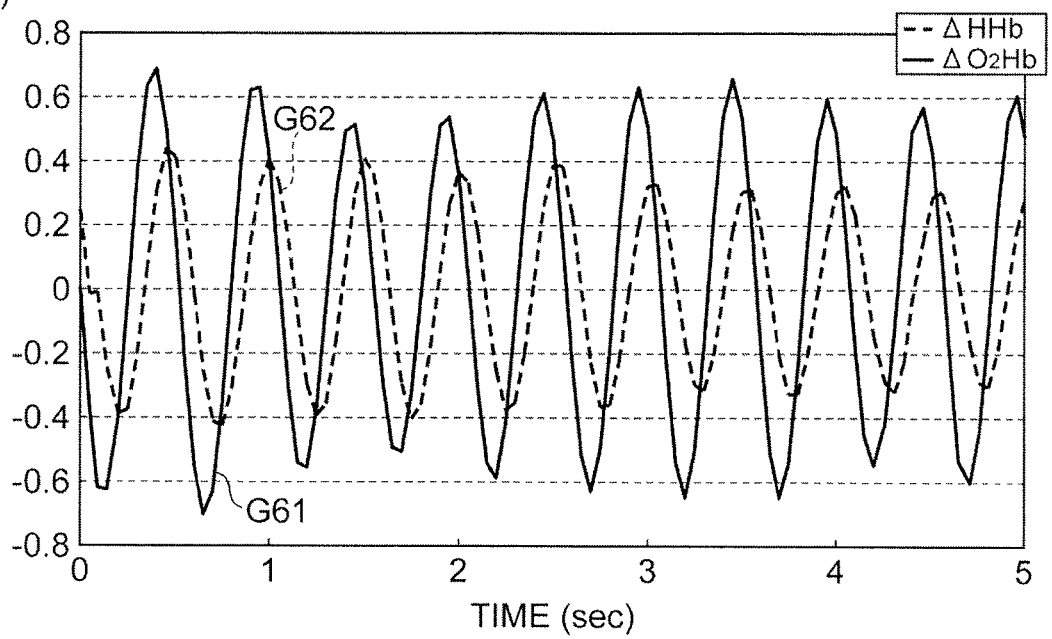
(b)
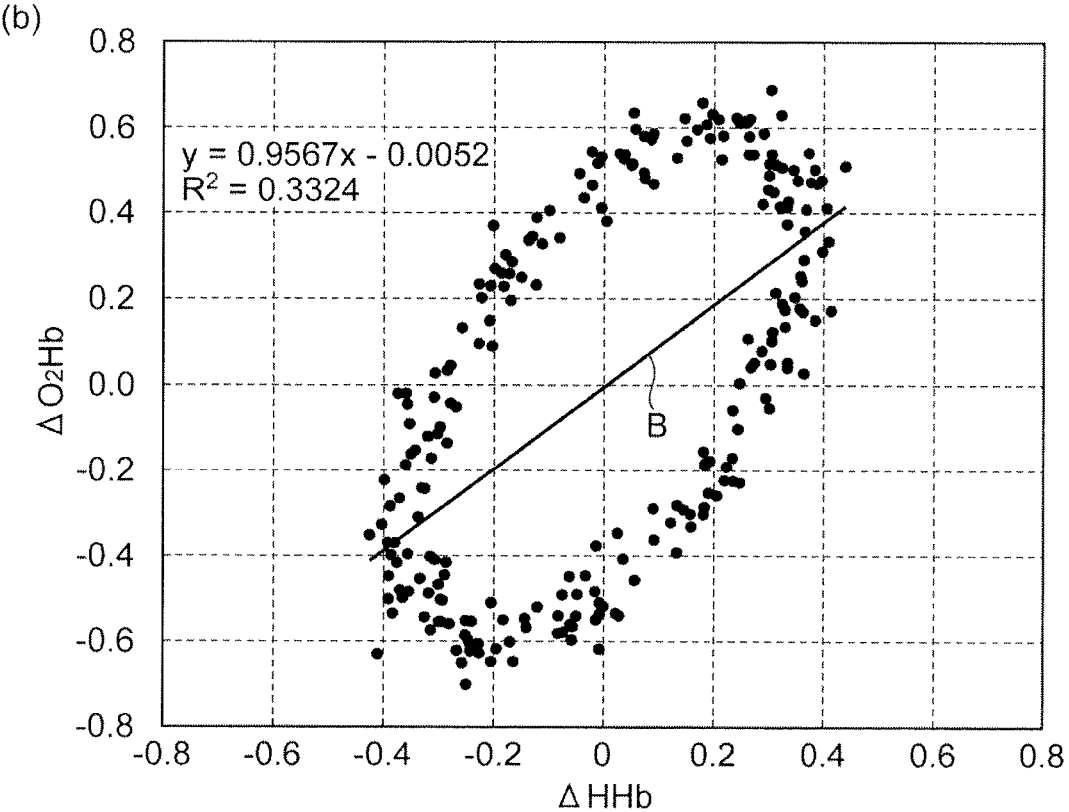

*Fig.11*
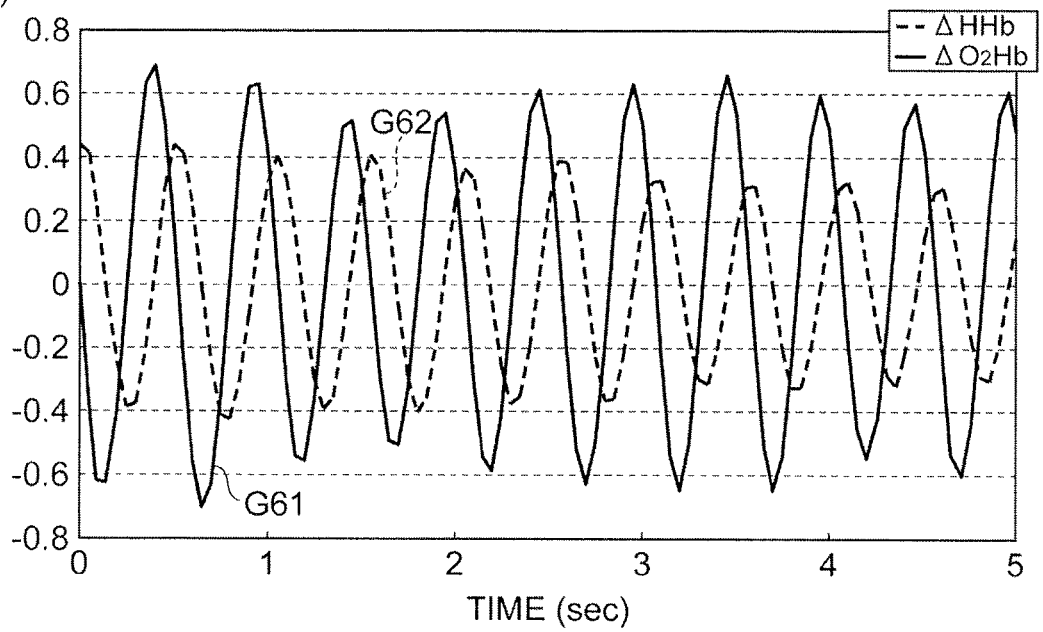
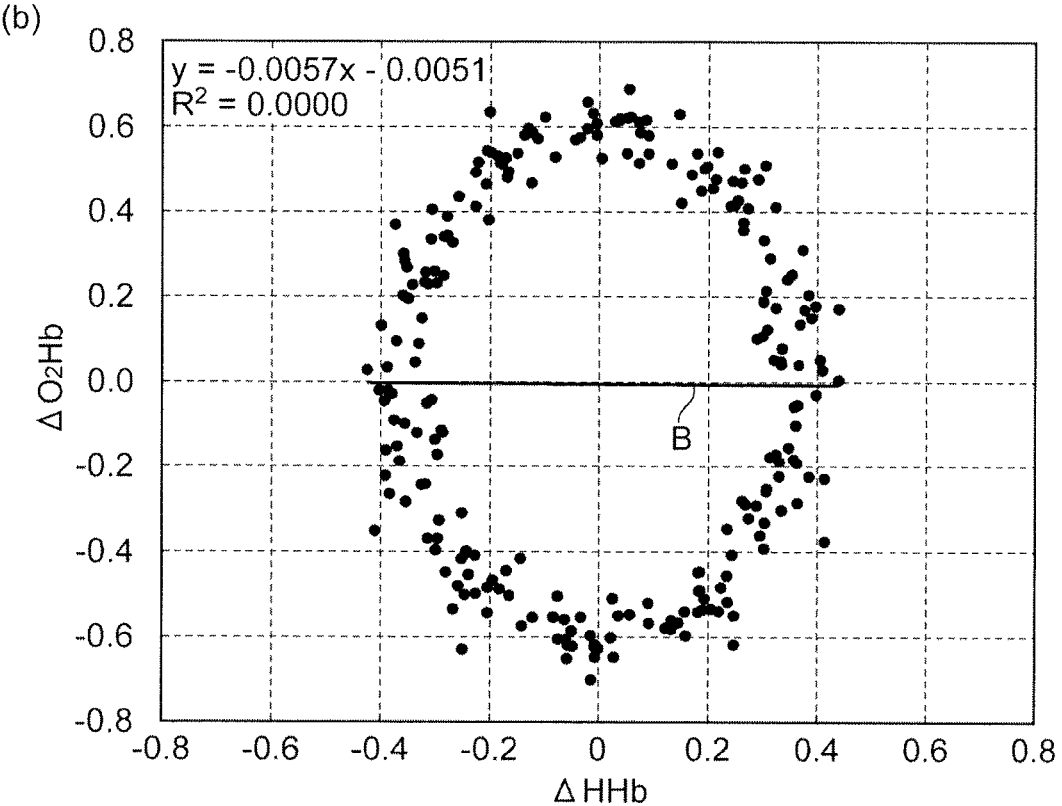

*Fig.12*
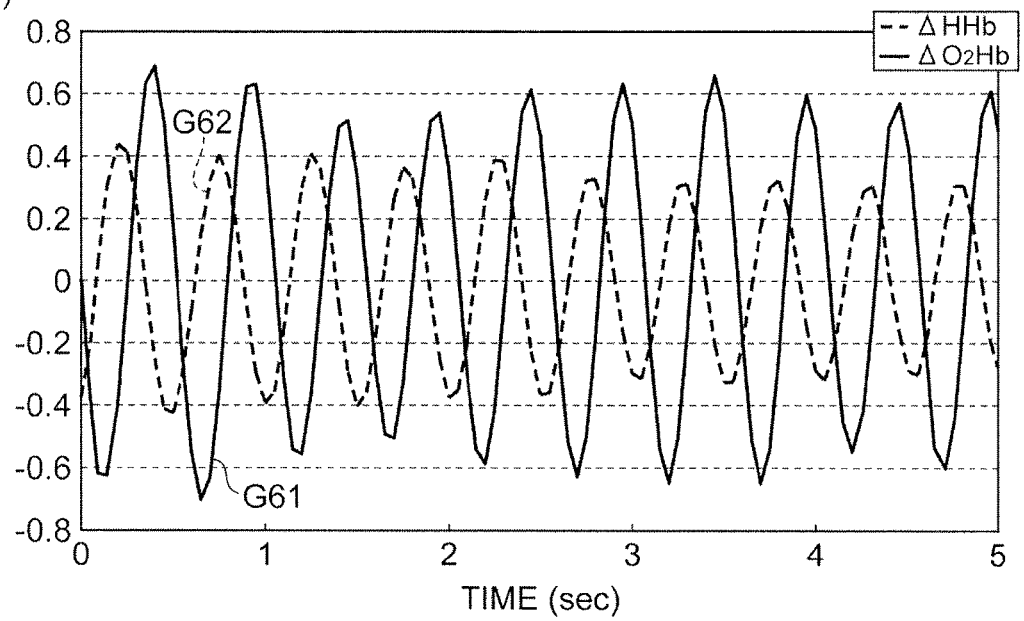
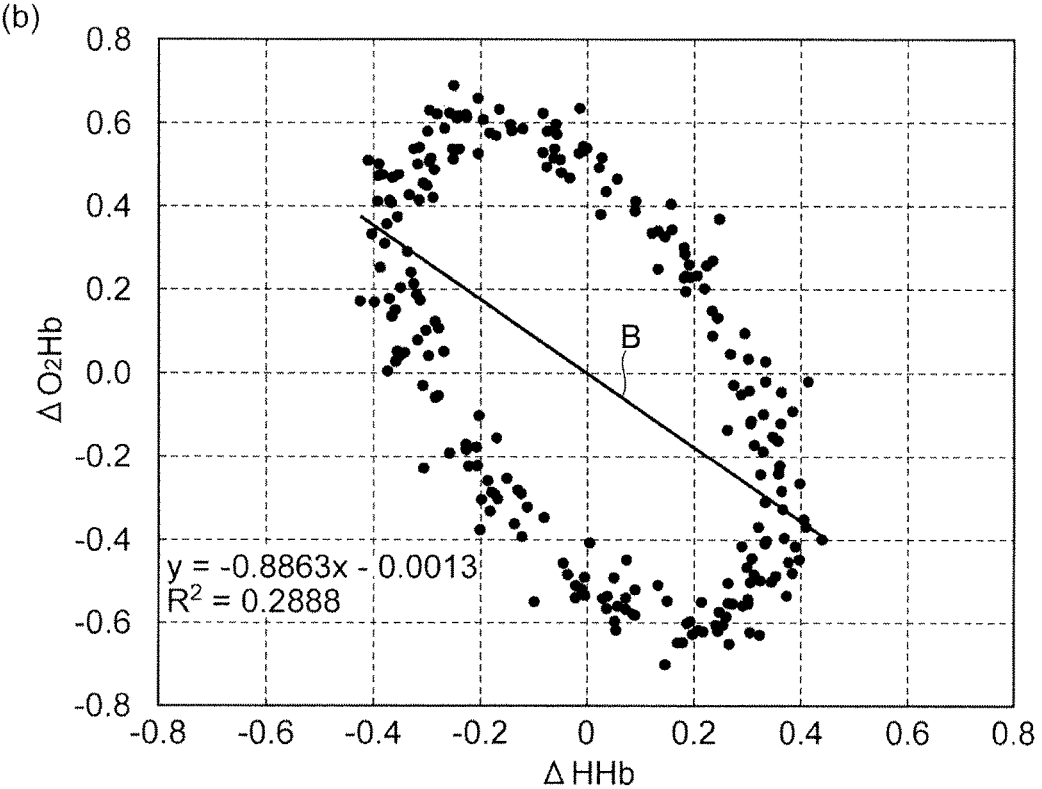

Fig.13
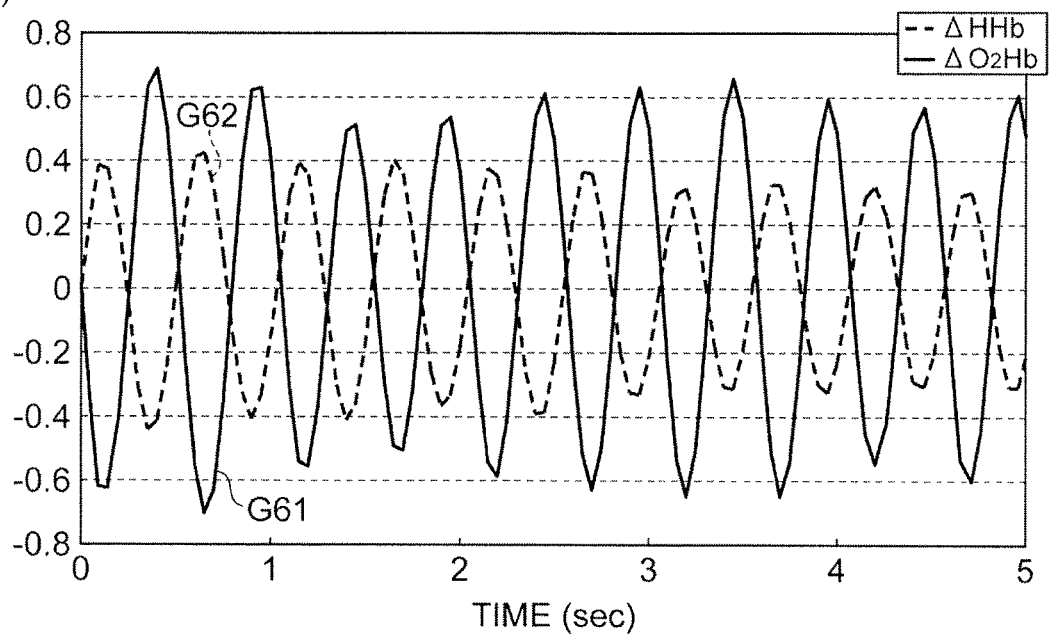
(a)
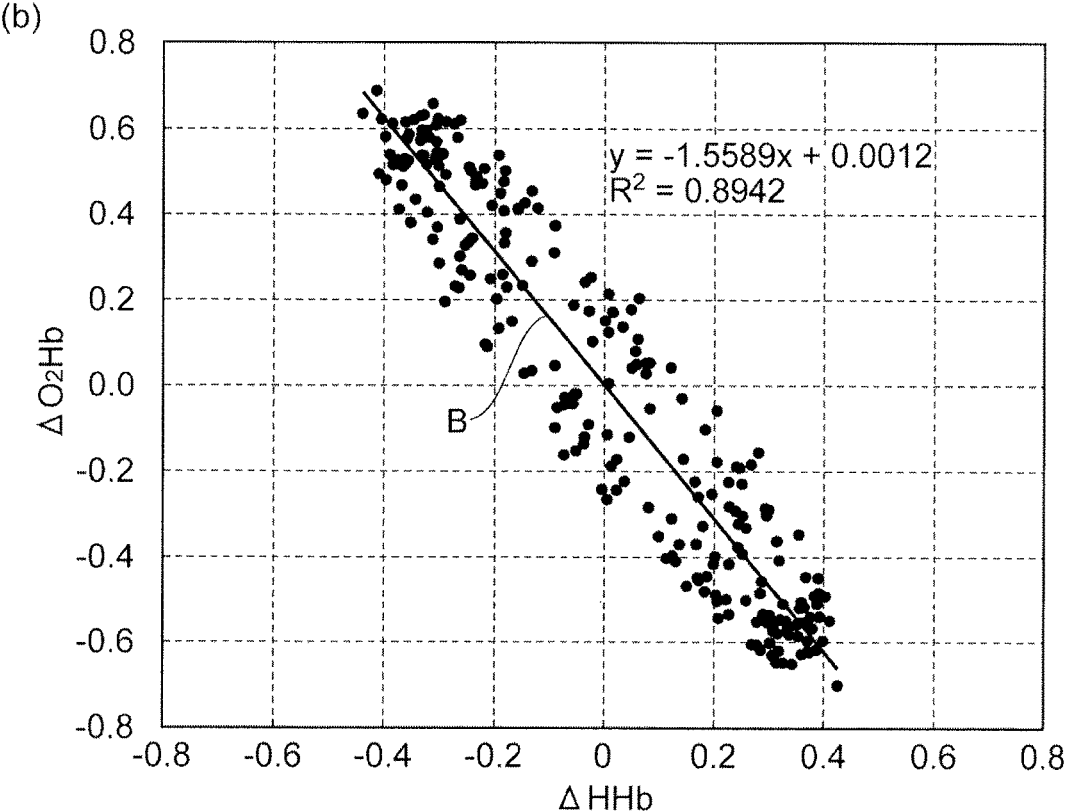
(b)

*Fig.15*
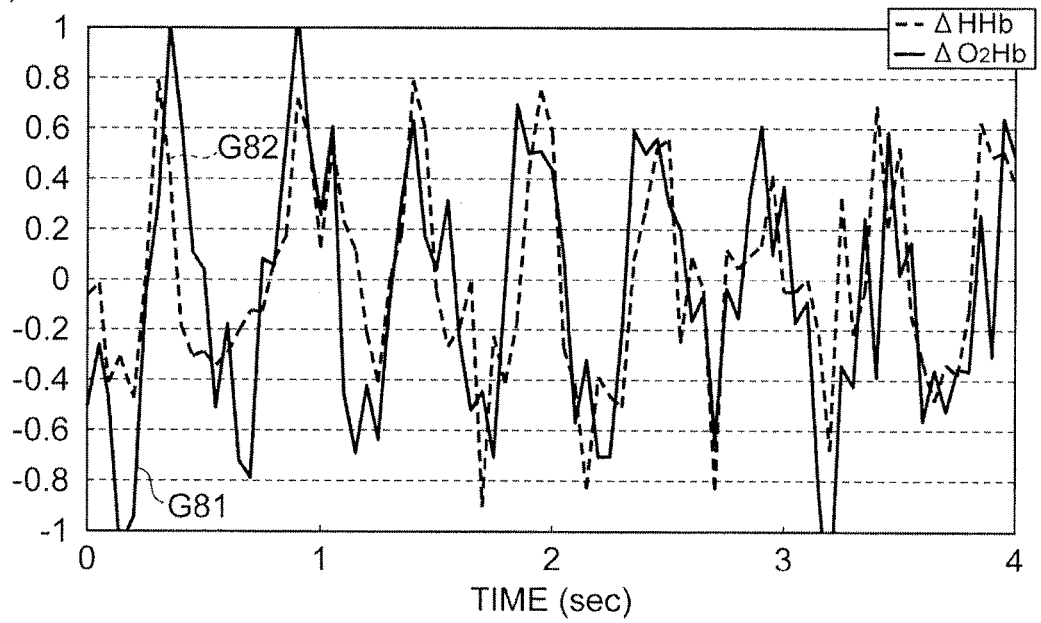
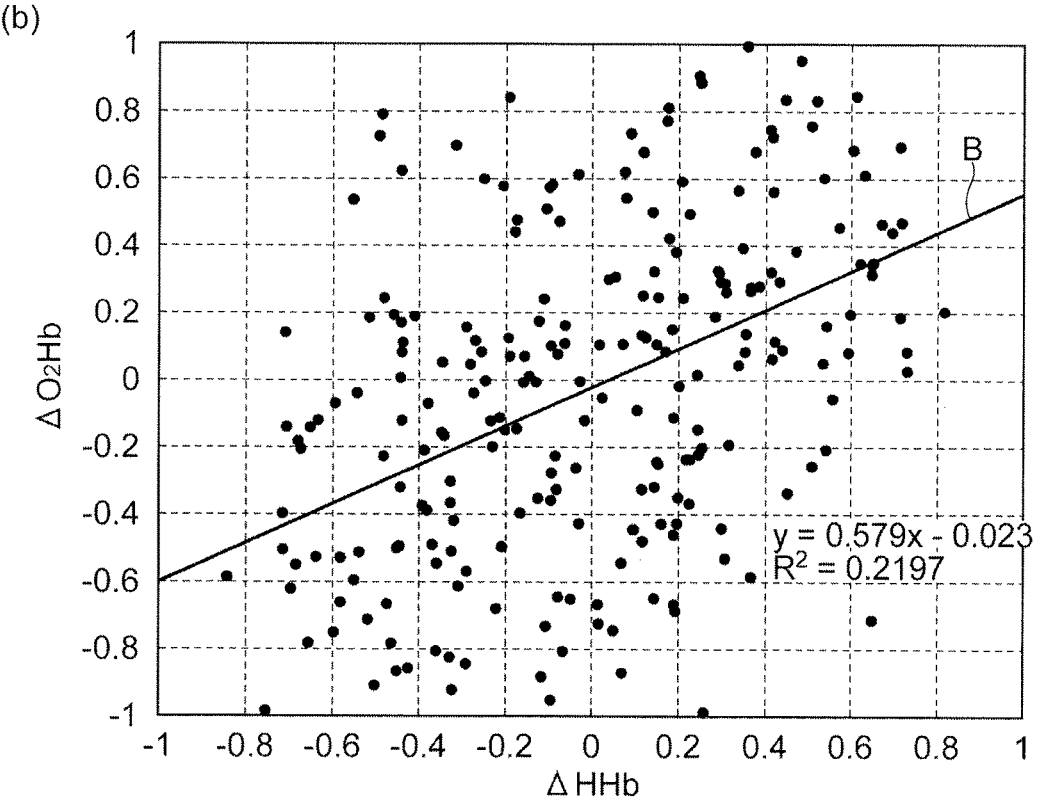

CONCENTRATION MEASUREMENT DEVICE AND CONCENTRATION MEASUREMENT METHOD

This is a divisional application of copending application Ser. No. 14/377,931, having a § 371 date of Aug. 11, 2014, which is a national stage filing based on PCT International Application No. PCT/JP2012/083474 filed on Dec. 25, 2012. The copending application Ser. No. 14/377,931 is incorporated by reference herein in its entirety.

TECHNICAL FIELD

The present invention relates to a concentration measurement apparatus and a concentration measurement method.

BACKGROUND ART

An example of a device for noninvasively measuring hemoglobin concentration information inside a living body is described in Patent Document 1. With this device, light is made incident inside the living body, and thereafter, light scattered inside the living body is detected by each of a plurality of photodiodes. Then, based on the intensities of the detected light components, a rate of change of the detected light amount in the direction of distance from the light incidence point is calculated. Hemoglobin oxygen saturation is calculated based on a predetermined relationship of the rate of change of the detected light amount and the light absorption coefficient. Also, based on a predetermined relationship of the temporal change of the rate of change of the detected light amount and the temporal change of the light absorption coefficient, respective concentration changes of oxygenated hemoglobin ($O_2Hb$), deoxygenated hemoglobin (HHb), and total hemoglobin (cHb) are calculated.

CITATION LIST

Patent Literature

Patent Document 1: Japanese Patent Application Laid-Open No, H7-255709

Non Patent Literature

Non-Patent Document 1: Susumu Suzuki, et al., "Tissue oxygenation monitor using NIR spatially resolved spectroscopy," Proceedings of SPIE 3597, pp. 582-592

SUMMARY OF INVENTION

Technical Problem

The primary patients in the emergency medical field in recent years are those suffering cardiopulmonary arrest outside a hospital. The number of out-of-hospital cardiopulmonary arrest persons exceeds 100 thousand per year, and emergency medical care of these persons is a major social demand. An essential procedure for out-of-hospital cardiopulmonary arrest persons is chest compression performed in combination with artificial respiration. Chest compression is an act where the lower half of the sternum is cyclically compressed by another person's hands to apply an artificial pulse to the arrested heart. A primary object of chest compression is to supply blood oxygen to the brain of the cardiopulmonary arrest person. Whether or not chest compression is being performed appropriately thus has a large influence on the life or death of the cardiopulmonary arrest person. Methods and devices that are useful for objectively judging whether or not chest compression is being performed appropriately are thus being demanded.

For example, measurement of a relative change amount of oxygenated hemoglobin concentration in the head at a frequency sufficiently higher than the heartbeat frequency using a concentration measurement apparatus that uses near-infrared light reveals that, in chest compression, certain changes occur in the oxygenated hemoglobin concentration and the deoxygenated hemoglobin concentration of the interior of the head (that is, the brain) each time the sternum is compressed cyclically. This phenomenon is considered to be due to an increase in blood flow within the brain by the chest compression, and may be usable as a material for objectively judging whether or not chest compression is being performed appropriately.

Here, to improve the reliability of calculation (for example, calculation of oxygen saturation) using the oxygenated hemoglobin concentration and deoxygenated hemoglobin concentration determined using near-infrared light, it is important for these hemoglobin concentrations to vary in the same phase mutually and in synchronization with the timing of chest compression. However, according to observations by the present inventors, although the concentrations vary in the same phase in the case of spontaneous heartbeat, these do not necessarily vary in the same phase in the case of chest compression of a cardiopulmonary arrest person. This is because, whereas in spontaneous heartbeat, a backflow prevention valve operates functionally due to the systematic contraction and expansion of the left and right atriums and ventricles and blood is fed unidirectionally from the vena cava to the aorta, in chest compression, blood flow is caused by pressing of the entire arrested heart and therefore blood transmission in the reverse direction from the vena cava occurs readily and becomes a cause of a shift between the phase of the oxygenated hemoglobin concentration and the phase of the deoxygenated hemoglobin concentration in the head.

Under such circus stances, the accuracy of calculation using the oxygenated hemoglobin concentration and the deoxygenated hemoglobin concentration is compromised and correct numerical values cannot be obtained for the amplitude of the total hemoglobin concentration and the oxygen saturation. Further, blood transmission in the reverse direction from the vena cava to the brain is, in itself, unfavorable. However, there were no conventional concentration measurement apparatuses that enable evaluation of such circumstances.

The present invention has been made in view of the above problem, and an object thereof is to provide a concentration measurement apparatus and a concentration measurement method that enable evaluation of the accuracy of calculation and the possibility of reverse direction blood transmission from the vena cava to the head based on the phase shift between the oxygenated hemoglobin concentration and the deoxygenated hemoglobin concentration.

Solution to Problem

In order to solve the above-described problem, a concentration measurement apparatus according to the present invention is a concentration measurement apparatus for measuring temporal relative change amounts of oxygenated hemoglobin concentration and deoxygenated hemoglobin concentration, that vary due to repetition of chest compression, in a head, and includes a light incidence section making measurement light incident on the head, a light detection section detecting the measurement light that has propagated through the interior of the head and generating a detection signal in accordance with the intensity of the detected measurement light, and a calculation section determining, based on the detection signal, a correlation coefficient of a first temporal relative change amount of the oxygenated hemoglobin concentration and a second temporal relative change amount of the deoxygenated hemoglobin concentration and a polarity of a slope of a regression line of the first relative change amount and the second relative change amount.

Further, a concentration measurement method according to the present invention is a concentration measurement method of measuring temporal relative change amounts of oxygenated hemoglobin concentration and deoxygenated hemoglobin concentration, that vary due to repetition of chest compression, in a head, and includes a light incidence step of making measurement light incident on the head, a light detection step of detecting the measurement light that has propagated through the interior of the head and generating a detection signal in accordance with the intensity of the detected measurement light, and a calculation step of determining, based on the detection signal, a correlation coefficient of a first temporal relative change amount of the oxygenated hemoglobin concentration and a second temporal relative change amount of the deoxygenated hemoglobin concentration and a polarity of a slope of a regression line of the first relative change amount and the second relative change amount.

With the above-described concentration measurement apparatus and concentration measurement method, the temporal relative change amounts of the oxygenated hemoglobin concentration and the deoxygenated hemoglobin concentration are determined, and further, the correlation coefficient of the temporal relative change amount of the oxygenated hemoglobin concentration (the first relative change amount) and the temporal relative change amount of the deoxygenated hemoglobin concentration (the second relative change amount), and the polarity of the slope of the regression line of these relative change amounts are determined in the calculation section or the calculation step. The correlation coefficient and the polarity of the slope of the regression line accurately express the shift between the phase of the oxygenated hemoglobin, concentration and the phase of the deoxygenated hemoglobin concentration. That is, when the phase shift is in a range of 0° to 90°, the polarity of the slope of the regression line is positive, and the value of the correlation coefficient decreases with an increase in the phase shift. Also, when the phase shift is in a range of 90° to 180°, the polarity of the slope of the regression line is negative, and the value of the correlation coefficient increases with an increase in the phase shift.

Therefore, by referring to the polarity of the slope of the regression line and the magnitude of the correlation coefficient together, the shift between the phase of the oxygenated hemoglobin concentration and the phase of the deoxygenated hemoglobin concentration can be made known accurately. That is, with the above-described concentration measurement apparatus and concentration measurement method, the accuracy of calculation of the amplitude of the total hemoglobin concentration and the oxygen saturation and the possibility of reverse direction blood transmission from the vena cava to the head can be evaluated easily based on the phase shift between the oxygenated hemoglobin concentration and the deoxygenated hemoglobin concentration.

Advantageous Effects of Invention

In accordance with the concentration measurement apparatus and concentration measurement method according to the present invention, the accuracy of calculation and the possibility of reverse direction blood transmission from the vena cava to the head can be evaluated based on the phase shift between the oxygenated hemoglobin concentration and the deoxygenated hemoglobin concentration.

BRIEF DESCRIPTION OF DRAWINGS

FIG. 2 includes (a) a plan view of a configuration of a probe, and (b) a sectional side view taken along line II-II of (a).

FIG. 9 includes (a) a graph of measured values of time series data of temporal relative change amounts ($\Delta O_2 Hb$, $\Delta HHb$), and (b) a scatter diagram of the temporal relative change amounts ($\Delta O_2 Hb$, $\Delta HHb$) corresponding to (a).

FIG. 10 includes (a) a graph of measured values of time series data of temporal relative change amounts ($\Delta O_2 Hb$, $\Delta HHb$), and (b) a scatter diagram of the temporal relative change amounts ($\Delta O_2 Hb$, $\Delta HHb$) corresponding to (a).

FIG. 11 includes (a) a graph of measured values of time series data of temporal relative change amounts ($\Delta O_2 Hb$, $\Delta HHb$), and (b) a scatter diagram of the temporal relative change amounts ($\Delta O_2 Hb$, $\Delta HHb$) corresponding to (a).

FIG. 12 includes (a) a graph of measured values of time series data of temporal relative change amounts ($\Delta O_2 Hb$, $\Delta HHb$), and (b) a scatter diagram of the temporal relative change amounts ($\Delta O_2 Hb$, $\Delta HHb$) corresponding to (a).

FIG. 13 includes (a) a graph of measured values of time series data of temporal relative change amounts ($\Delta O_2 Hb$, $\Delta HHb$), and (b) a scatter diagram of the temporal relative change amounts ($\Delta O_2 Hb$, $\Delta HHb$) corresponding to (a).

FIG. 15 includes (a) a graph of time series data resulting from mixing noise in the temporal relative change amounts ($\Delta O_2Hb$, $\Delta HHb$) shown in FIG. 9, and (b) a scatter diagram of the temporal relative change amounts ($\Delta O_2Hb$, $\Delta HHb$) corresponding to (a).

DESCRIPTION OF EMBODIMENTS

Hereinafter, an embodiment of a concentration measurement apparatus and a concentration measurement method according to the present invention will be described in detail with reference to the accompanying drawings. In the description of the drawings, elements that are the same are provided with the same reference symbols, and redundant description is omitted.

Figure 1:
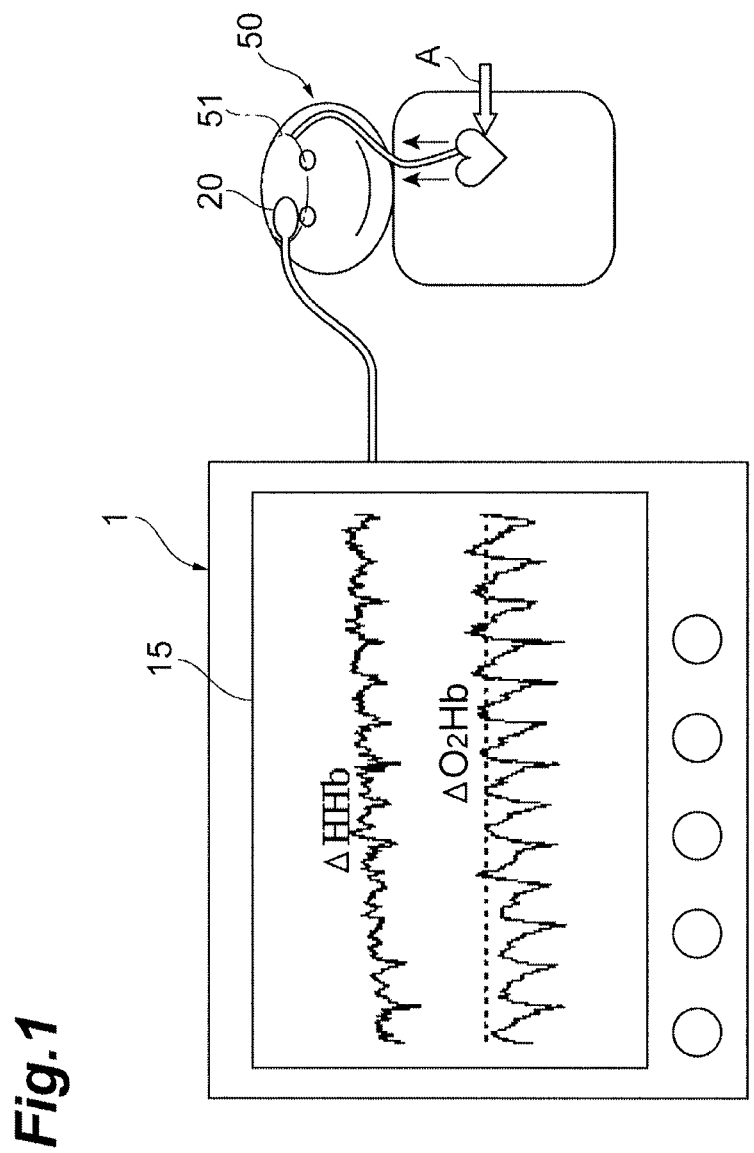
FIG. 1 is a conceptual diagram of a concentration measurement apparatus according to an embodiment.

FIG. 1 is a conceptual diagram of a concentration measurement apparatus 1 according to an embodiment of the present invention. To provide material for objectively judging whether or not chest compression (arrow A in the figure) is being performed appropriately on a cardiopulmonary arrest person 50, the concentration measurement apparatus 1 measures respective temporal variations (relative change amounts) from initial amounts of total hemoglobin (cHb) concentration, oxygenated hemoglobin ($O_2Hb$) concentration, and deoxygenated hemoglobin (HHb) concentration of the head 51 that vary due to repeated chest compression, and displays the measurement results on a display section 15 to notify a person performing the chest compression.

The concentration measurement apparatus 1 makes light beams of predetermined wavelengths ($\lambda_1$, $\lambda_2$, and $\lambda_3$) be incident on a predetermined light incidence position from a probe 20 fixed to the head 51, and detects intensities of light components emitted from predetermined light detection positions on the head 51 to examine the effects of the oxygenated hemoglobin ($O_2Hb$) and the deoxygenated hemoglobin (HHb) on the light, and based thereon, repeatedly calculates the temporal relative change amounts of the oxygenated hemoglobin ($O_2Hb$) and the deoxygenated hemoglobin (HHb). Also, the apparatus applies a filtering process to time series data that are the calculation results, and thereby removes low frequency components. A short-cycle temporal variation component due to the repetition of chest compression is thereby extracted and subsequent necessary processes are performed. The temporal variation component can also be displayed in a more visible manner. As the light of predetermined wavelengths, for example, near-infrared light is used.

(a) in FIG. 2 is a plan view of a configuration of a probe 20. Further, (b) in FIG. 2 is a sectional side view taken along line II-II of (a) in FIG. 2. The probe 20 has a light incidence section 21 and a light detection section 22. The light incidence section 21 and the light detection section 22 are disposed with an interval, for example, of 5 cm from each other, and are practically integrated by a holder 23 made of flexible, black silicone rubber. Here, the interval suffices to be not less than approximately 3 to 4 cm.

The light incidence section 21 includes an optical fiber 24 and a prism 25, and has a structure that makes the measurement light, transmitted from a main unit section 10 of the concentration measurement apparatus 1, incident substantially perpendicularly on the skin of the head. The measurement light is, for example, a laser light beam of pulse form, and is transmitted from the main unit section 10.

The light detection section 22 detects measurement light components that have propagated through the interior of the head, and generates detection signals that are in accordance with the intensities of the measurement light components. The light detection section 22 is, for example, a one-dimensional photosensor having an array of N photodetection elements 26 aligned in a direction of distance from the light incidence section 21. Also, the light detection section 22 further has a pre-amplifier section 27 that integrates and amplifies photocurrents output from the photodetection elements 26. By this configuration, weak signals can be detected with high sensitivity to generate detection signals, and the signals can be transmitted via a cable 28 to the main unit section 10. Here, the light detection section 22 may instead be a two-dimensional photosensor, or may be configured by a charge-coupled device (CCD). The probe 20 is, for example, fixed by an adhesive tape or a stretchable band, etc., onto a forehead portion without hair.

Figure 3:
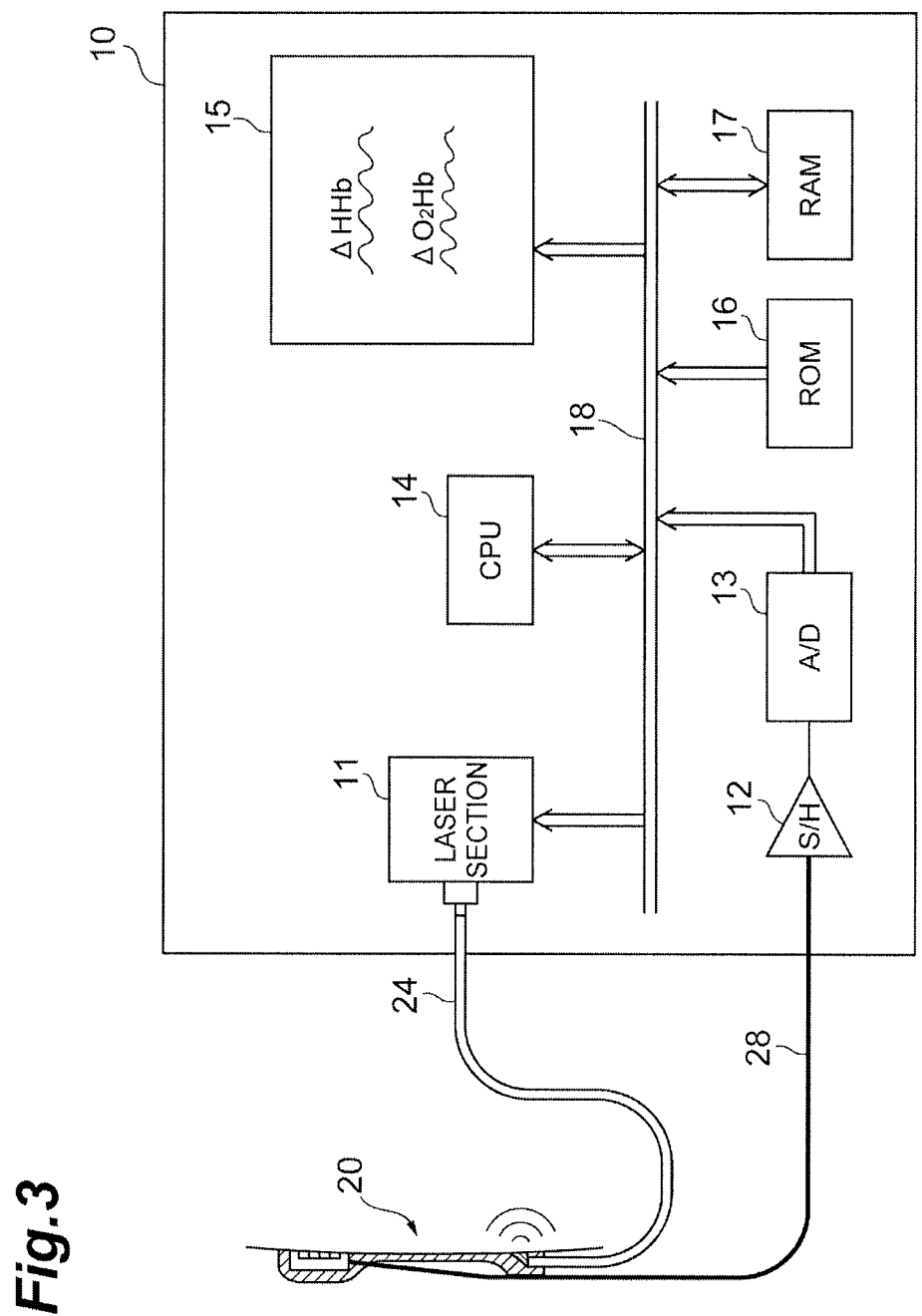
FIG. 3 is a block diagram of a configuration example of the concentration measurement apparatus.

FIG. 3 is a block diagram of a configuration example of the concentration measurement apparatus 1. The concentration measurement apparatus 1 shown in FIG. 3 includes the main unit section 10 in addition to the probe 20 described above. The main unit section 10 includes a light emitting section 11, a sample hold circuit 12, an A/D converter circuit 13, a CPU 14, a display section 15, a ROM 1.6, a RAM 17, and a data bus 18.

The light emitting section 11 is configured by a laser diode and a circuit that drives the laser diode. The light emitting section 11 is electrically connected to the data bus 18 and receives an instruction signal for instructing the driving of the laser diode from the CPU 14 that is similarly electrically connected to the data bus 18. The instruction signal contains information on the light intensity, wavelength (for example, a wavelength among wavelengths $\lambda_1$, $\lambda_2$, and $\lambda_3$), etc., of the laser light output from the laser diode. The light emitting section 11 drives the laser diode based on the instruction signal received from the CPU 14 and outputs laser light to the probe 20 via the optical fiber 24. Here, the light emitting element of the light emitting section 11 does not have to be a laser diode, and suffices to be an element that can successively output light beams of a plurality of wavelengths in the near-infrared region. Also, an LED or other light emitting diode that is built into the probe 20 may be used as the light incidence section 21.

The sample hold circuit 12 and the A/D converter circuit 13 input the detection signals transmitted via the cable 28 from the probe 20 and perform holding and conversion of the signals to digital signals that are then output to the CPU 14. The sample hold circuit 12 simultaneously holds the values of N detection signals. The sample hold circuit 12 is electrically connected to the data bus 18, and receives a sample signal, indicating the timing of holding of the detection signals, from the CPU 14 via the data bus 18. Upon receiving the sample signal, the sample hold circuit 12 simultaneously holds N detection signals input from the probe 20. The sample hold circuit 12 is electrically connected to the A/D converter circuit 13, and outputs each of the held N detection signals to the A/D converter circuit 13.

The A/D converter circuit 13 is means for converting the detection signals from analog signals to digital signals. The A/D convertor circuit 13 successively converts the N detection signals received from the sample hold circuit 12 into digital signals. The A/D convertor circuit 13 is electrically connected to the data bus 18 and outputs the converted detection signals to the CPU 14 via the data bus 18.

The CPU 14 is a calculation section in the present embodiment and, based on the detection signals received from the A/D converter circuit 13, calculates the temporal relative change amount of the oxygenated hemoglobin concentration ($\Delta O_2Hb$, first relative change amount) and the temporal relative change amount of the deoxygenated hemoglobin concentration ($\Delta HHb$, second relative change amount) that are contained in the interior of the head, and further calculates, as necessary, the temporal relative change amount of the total hemoglobin concentration (ΔcHb), which is the sum of these amounts. Further, the CPU 14 applies a filtering process to the temporal relative change amounts (ΔO₂Hb, ΔHHb, ΔcHb) to remove frequency components less than a predetermined frequency from frequency components contained in the amounts to thereby extract temporal variation components due to repetition of chest compression. The CPU 14 transmits time series data that indicate the calculated temporal relative change amounts (ΔO₂Hb, ΔHHb, ΔcHb) to the display section 15 via the data bus 18. A method of calculating the temporal relative change amounts (ΔO₂Hb, ΔHHb, ΔcHb) based on the detection signals and a method of the filtering process shall be described later. The display section 15 is electrically connected to the data bus 18, and displays the results transmitted from the CPU 14 via the data bus 18.

Also, the CPU 14 further determines a correlation coefficient of the temporal relative change amount of the oxygenated hemoglobin concentration (ΔO₂Hb) and the temporal relative change amount of the deoxygenated hemoglobin concentration (ΔHHb). Also, the CPU 14 further determines the polarity of the slope of a regression line in a scatter diagram of the temporal relative change amount of the oxygenated hemoglobin concentration (ΔO₂Hb) and the temporal relative change amount of the deoxygenated hemoglobin concentration (ΔHHb). The methods of calculating the correlation coefficient and the polarity of the slope of the regression line shall be described later. The display section 15 displays the time series data that indicate the temporal relative change amounts (ΔO₂Hb, ΔHHb, ΔcHb) together with the value of the correlation coefficient and the polarity of the slope of the regression line. Or, the display section 15 may display other display elements (for example, a graph or icon, etc.) corresponding to the value of the correlation coefficient and the polarity of the slope of the regression line in place of these. Especially in regard to the correlation coefficient, it is preferable to display by at least one of a numeral and a graph.

Figure 4:
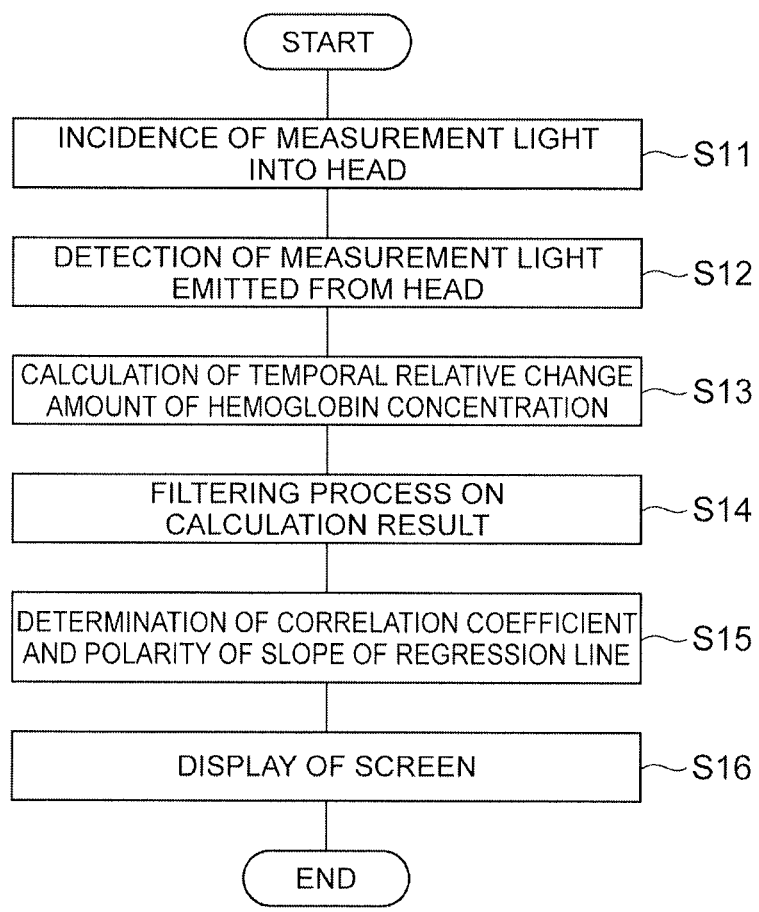
FIG. 4 is a flowchart of a concentration measurement method according to an embodiment.

The operation of the concentration measurement apparatus 1 shall now be described. In addition, the concentration measurement method according to the present embodiment shall be described. FIG. 4 is a flowchart of the concentration measurement method according to the present embodiment.

First, the light emitting section 11 successively outputs the laser light beams of wavelengths $\lambda_1$ to $\lambda_3$ based on the instruction signal from the CPU 14. The laser light beams propagate through the optical fiber 24, reach the light incidence position at the forehead portion, and enter inside the head from the light incidence position (light incidence step, S11). The laser light beam made to enter inside the head propagates while being scattered inside the head and being absorbed by measurement object components, and parts of the light reach the light detection positions of the forehead portion. The laser light components that reach the light detection positions are detected by the N photodetection elements 26 (light detection step, S12). Each photodetection element 26 generates a photocurrent in accordance with the intensity of the detected laser light component. These photocurrents are converted into voltage signals (detection signals) by the pre-amplifier section 27, and the voltage signals are transmitted to and held by the sample hold circuit 12 of the main unit section 10, and thereafter, converted into digital signals by the A/D converter circuit 13.

Figure 5:
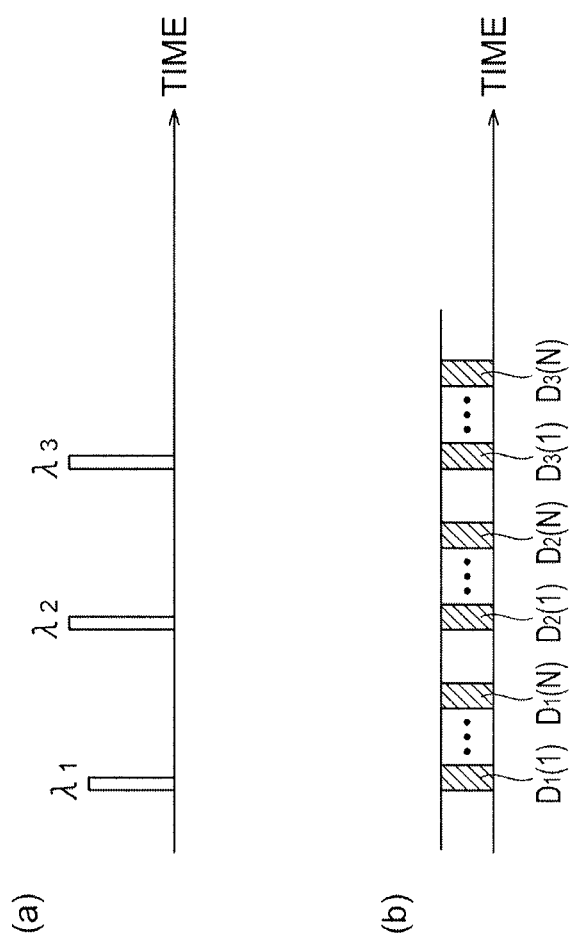
FIG. 5 includes (a) a diagram of incidence timings of laser light beams of wavelengths $\lambda_1$ to $\lambda_3$, and (b) a diagram of output timings of digital signals from an A/D converter circuit.

Here, (a) in FIG. 5 is a diagram of incidence timings of the laser light beams of wavelengths $\lambda_1$ to $\lambda_3$, and (b) in FIG. 5 is a diagram of output timings of the digital signals from the A/D converter circuit 13. As shown in FIG. 5, when the laser light of wavelength $\lambda_1$ is made incident, N digital signals $D_1(1)$ to $D_1(N)$ corresponding to the N photodetection elements 26 are obtained successively. Next, when the laser light of wavelength $\lambda_2$ is made incident, N digital signals $D_2(1)$ to $D_2(N)$ corresponding to the N photodetection elements 26 are obtained successively. Thus, (3×N) digital signals $D_1(1)$ to DAN are output from the A/D converter circuit 13.

Subsequently, the CPU 14 calculates the hemoglobin oxygen saturation (TOI) based on the digital signals D(1) to D(N). Also, the CPU 14 uses at least one digital signal from the digital signals D(1) to D(N) to calculate the temporal relative change amount (ΔO₂Hb) of the oxygenated hemoglobin concentration, the temporal relative change amount (ΔHHb) of the deoxygenated hemoglobin concentration, and the temporal relative change amount (ΔcHb) of the total hemoglobin concentration, which is the sum of these (calculation step, step S13). Then, of the frequency components contained in the relative change amounts (ΔcHb, ΔO₂Hb, ΔHHb), the frequency components less than the predetermined frequency are removed by a filtering process (calculation step, S14).

The "filtering process of removing frequency components less than a predetermined frequency" in the present embodiment refers to a process of decreasing the proportion of frequency components less than the predetermined frequency until the frequency component due to chest compression appears at a sufficiently recognizable level, and is not restricted to completely removing the frequency components less than the predetermined frequency.

The above-described calculation performed by the CPU 14 in the calculation steps S13 and S14 shall now be described in detail.

If $D_{\lambda 1}(T_0)$ to $D_{\lambda 3}(T_0)$ are values of the detection signals, respectively corresponding to the laser light wavelengths $\lambda_1$ to $\lambda_3$, at a time $T_0$ at a certain light detection position, and $D_{\lambda 1}(T_1)$ to $D_{\lambda 3}(T_1)$ are likewise values at a time $T_1$, the change amounts of the detected light intensities in the time $T_0$ to $T_1$ are expressed by the following formulas (1) to (3).

[Formula 1]
$$\Delta OD_1(T_1) = \log\left(\frac{D_{\lambda 1}(T_1)}{D_{\lambda 1}(T_0)}\right) \quad (1)$$

[Formula 2]
$$\Delta OD_2(T_1) = \log\left(\frac{D_{\lambda 2}(T_1)}{D_{\lambda 2}(T_0)}\right) \quad (2)$$

[Formula 3]
$$\Delta OD_3(T_1) = \log\left(\frac{D_{\lambda 3}(T_1)}{D_{\lambda 3}(T_0)}\right) \quad (3)$$

Here, in the formulas (1) to (3), $\Delta OD_1(T_1)$ is the temporal change amount of the detected light intensity of wavelength $\lambda_1$, $\Delta OD_2(T_1)$ is the change amount of the detected light intensity of wavelength $\lambda_2$, and $\Delta OD_3(T_1)$ is the temporal change amount of the detected light intensity of wavelength $\lambda_3$.

Further, if $\Delta O_2Hb(T_1)$ and $\Delta HHb(T_1)$ are the temporal relative change amounts of the concentrations of oxygenated hemoglobin and deoxygenated hemoglobin, respectively, in the period from time $T_0$ to time $T_1$, these can be determined by the following formula (4).

[Formula 4]

$$\begin{pmatrix} \Delta O_2Hb(T_1) \\ \Delta HHb(T_1) \end{pmatrix} = \begin{pmatrix} a_{11} & a_{12} & a_{13} \\ a_{21} & a_{22} & a_{23} \end{pmatrix} \begin{pmatrix} \Delta OD_1(T_1) \\ \Delta OD_2(T_1) \\ \Delta OD_3(T_1) \end{pmatrix} \quad (4)$$

Here, in the formula (4), the coefficients a11 to a23 are constants determined from absorbance coefficients of $O_2Hb$ and HHb for light components of wavelengths $\lambda_1$, $\lambda_2$, and $\lambda_3$. Also, the temporal relative change amount $\Delta cHb(T_1)$ of the total hemoglobin concentration in the head can be determined by the following formula (5).

[Formula 5]

$$\Delta cHb(T_1) = \Delta O_2Hb(T_1) + \Delta HHb(T_1) \quad (5)$$

The CPU 14 performs the above calculation on detection signals from one position among the N light detection positions to calculate the respective temporal relative change amounts ($\Delta O_2Hb$, $\Delta HHb$, $\Delta cHb$) of the oxygenated hemoglobin concentration, deoxygenated hemoglobin concentration, and total hemoglobin concentration. Further, the CPU 14 may perform, for example, any of the following filtering processes on the temporal relative change amounts ($\Delta O_2Hb$, $\Delta HHb$, $\Delta cHb$) that have thus been calculated.

(1) Filtering Process by a Digital Filter

Let X(n) be a data string related to a temporal relative change amount ($\Delta O_2Hb$, $\Delta HHb$, $\Delta cHb$) obtained at a predetermined cycle. Here, n is an integer. By multiplying the respective data of the data string X(n) by, for example, the following filter coefficients A(n), with n=0 being the time center, a non-recursive linear phase digital filter is realized.

A(0)=3/4
A(3)=A(−3)=−1/6
A(6)=A(−6)=−1/8
A(9)=A(−9)=−1/12

To describe in further detail, a delay operator for the data string X(n) is represented by the following formula (6). Here, f is the time frequency (units: 1/sec). Also, ω is the angular frequency and ω=2πf. T is the cycle at which the data string X(n) is obtained and is set, for example, to a cycle of 1/20 seconds for measuring a variation waveform at approximately 150 times per minute (2.5 Hz).

[Formula 6]

$$e^{j\omega nT} = \cos(\omega nT) + j\sin(\omega nT)$$

$$e^{-j\omega nT} = \cos(\omega nT) - j\sin(\omega nT) \quad (6)$$

In this case, the digital filter characteristics when the above-described filter coefficients A(n) are used are described by the following formula (7).

[Formula 7]

$$R(\omega) = 3/4 - 1/6(e^{-3j\omega T} + e^{+3j\omega T}) - 1/8(e^{-6j\omega T} + e^{+6j\omega T}) - 1/12(e^{-9j\omega T} + e^{+9j\omega T}) = 3/4 - 1/3\cos(3\omega T) - 1/4\cos(6\omega T) - 1/6\cos(9\omega T) \quad (7)$$

The digital filter is thus expressed by a product-sum operation of the data string X(n) and the corresponding coefficients. Further, by converting the time frequency f in formula (7) to a time frequency F per minute (units: 1/min), the following formula (8) is obtained.

[Formula 8]

$$R(F) = 3/4 - 1/3\cos(3\pi/600F) - 1/4\cos(6\pi/600F) - 1/6\cos(9\pi/600F) \quad (8)$$

Figure 6:
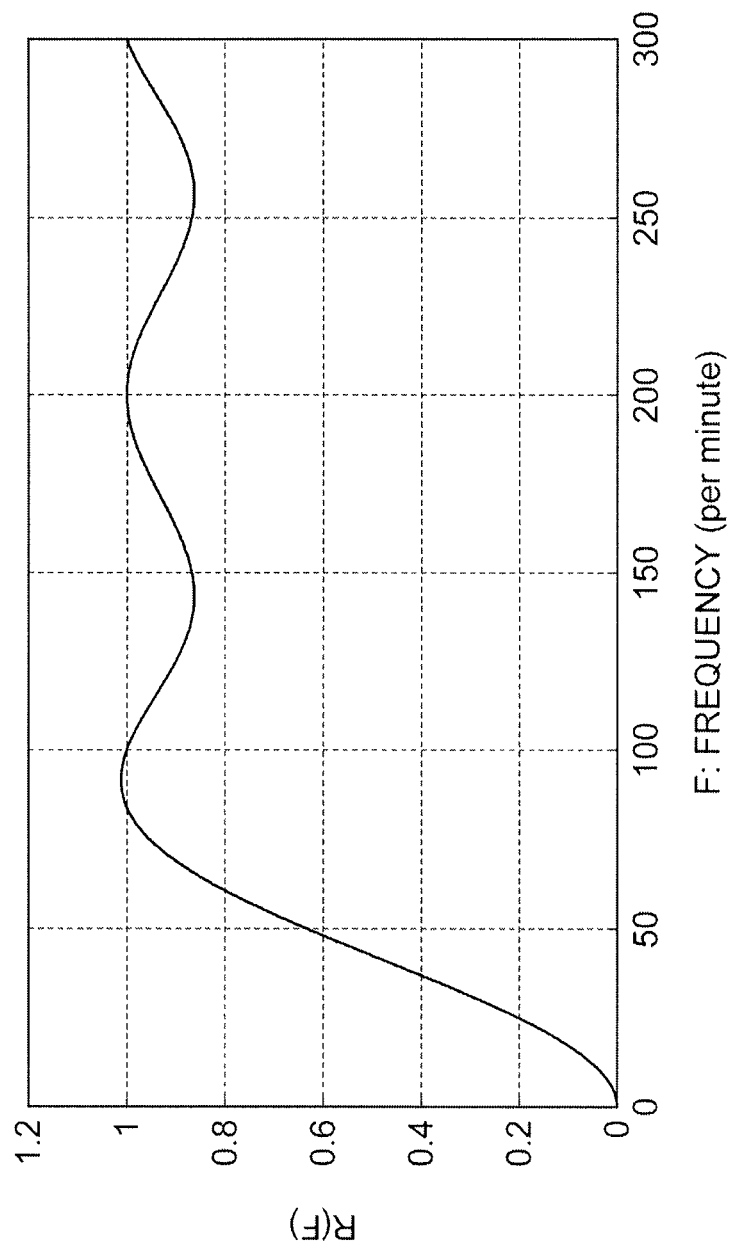
FIG. 6 is a graph of filter characteristics of a digital filter.
Figure 7:
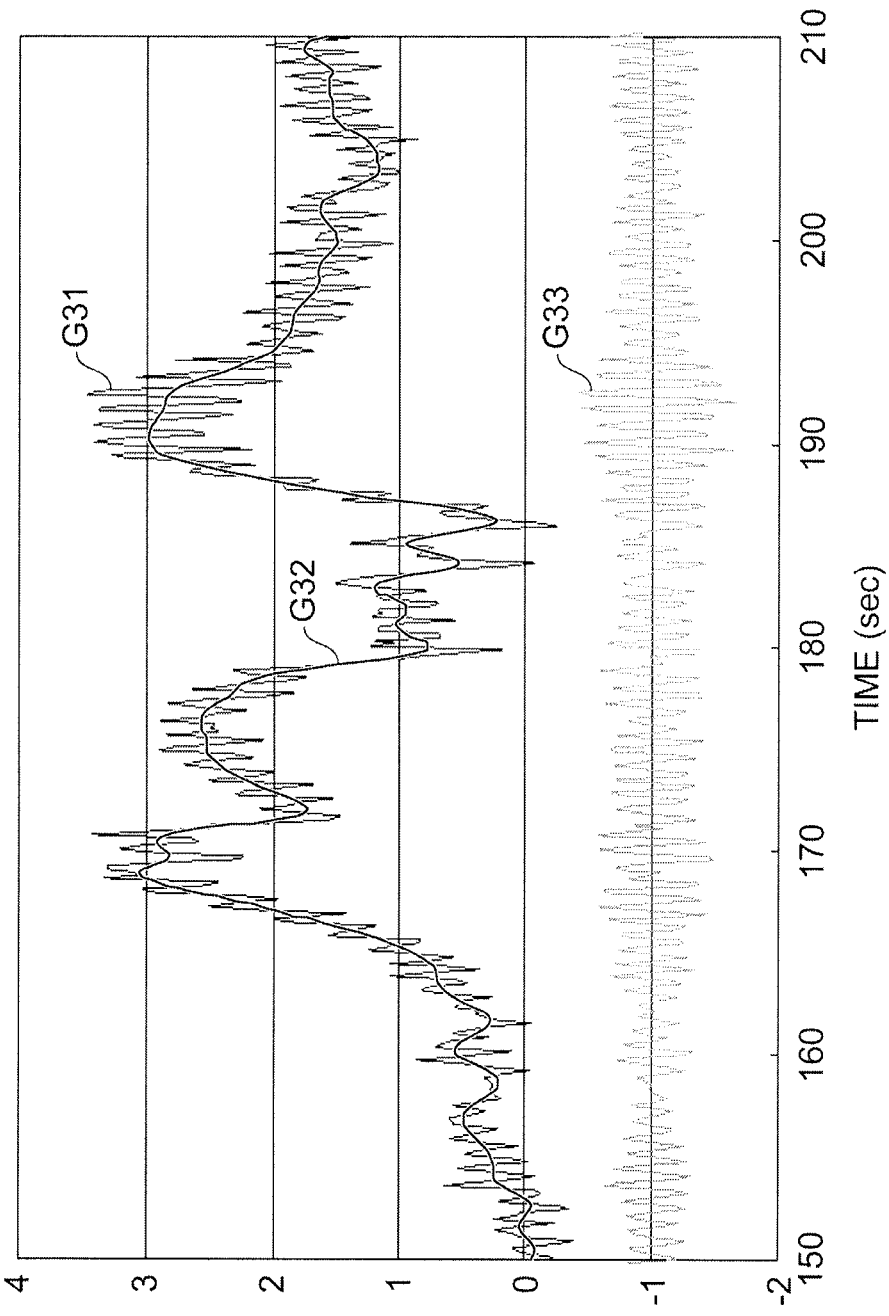
FIG. 7 is a graph of results of using the digital filter having the characteristics shown in FIG. 6 to remove frequency components less than a predetermined frequency from frequency components contained in a temporal relative change amount ($\Delta O_2 Hb$) of oxygenated hemoglobin to thereby extract a temporal variation component due to a spontaneous heartbeat that simulates the repetition of chest compression.

FIG. 6 is a graph of R(F), and shows the filter characteristics of the digital filter. In FIG. 6, the horizontal axis represents the number of heartbeats per minute, and the vertical axis represents the value of R(F). Further, FIG. 7 is a graph of results of using the digital filter shown in FIG. 6 to remove (reduce) frequency components less than the predetermined frequency from the frequency components contained in the temporal relative change amount ($\Delta O_2Hb$) of oxygenated hemoglobin to extract a temporal variation component due to a spontaneous heartbeat that simulates the repetition of chest compression. In FIG. 7, a graph G31 represents the relative change amount ($\Delta O_2Hb$) before the filtering process, a graph G32 represents the long cycle components (frequency components less than the predetermined frequency) contained in the relative change amount ($\Delta O_2Hb$) before the filtering process, and a graph G33 represents the relative change amount ($\Delta O_2Hb$) after the filtering process. As shown in FIG. 7, by the above digital filter, the temporal variation component due to the spontaneous heartbeat or the repetition of chest compression can be extracted favorably.

(2) Filtering Process by a Smoothing Calculation (Least-Square Error Curve Fitting)

A least square error curve fitting using a high-order function (for example, a fourth-order function) is performed on a data string X(n), within the above-described data string X(n), that is obtained in a predetermined time (for example, 3 seconds, corresponding to 5 beats) before and after n=0 as the time center. The constant term of the high-order function obtained is then deemed to be a smoothed component (frequency component less than the predetermined frequency) at n=0. That is, by subtracting the smoothed frequency component from the original data X(0), the frequency component less than the predetermined frequency can be removed from the frequency components contained in the relative change amount to separate/extract the temporal variation component due to repeated chest compression.

Figure 8:
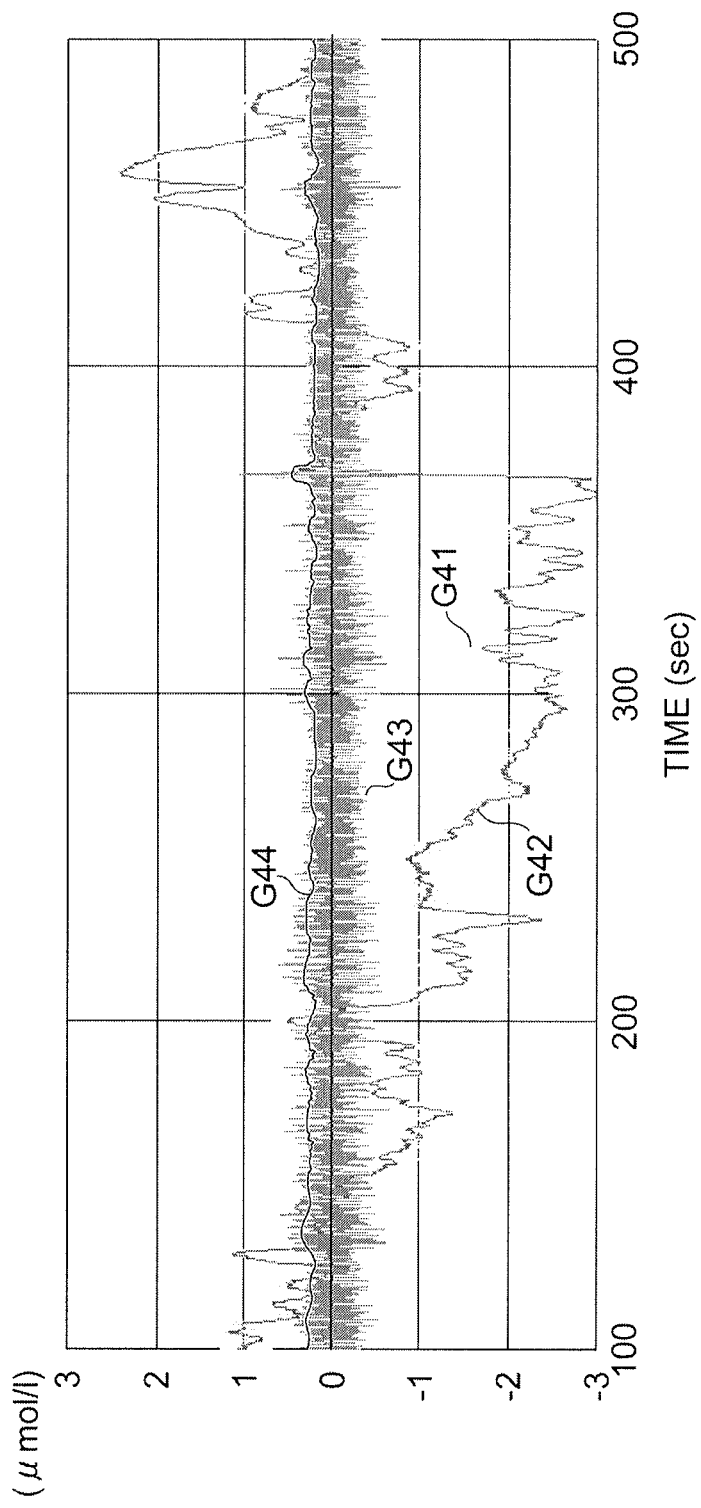
FIG. 8 is a graph of results of using a filtering process by smoothing to remove frequency components less than a predetermined frequency from frequency components contained in a temporal relative change amount ($\Delta cHb$) of total hemoglobin to thereby extract a temporal variation component due to a spontaneous heartbeat that simulates the repetition of chest compression.

FIG. 8 is a graph of results of using such a filtering process to remove (reduce) frequency components less than the predetermined frequency from the frequency components contained in the temporal relative change amount ($\Delta cHb$) of the total hemoglobin to extract a temporal variation component due to a spontaneous heartbeat that simulates the repetition of chest compression. In FIG. 8, a graph G41 represents the relative change amount ($\Delta cHb$) before the filtering process, a graph G42 represents the long cycle components (frequency components less than the predetermined frequency) contained in the relative change amount ($\Delta cHb$) before the filtering process, a graph G43 represents the relative change amount ($\Delta cHb$) after the filtering process, and a graph G44 indicates the 5-second average amplitudes in the relative change amount ($\Delta cHb$) after the filtering process. As shown in FIG. 8, by the filtering process by the above-described smoothing calculation, the temporal variation component due to the spontaneous heartbeat or the repetition of chest compression can be extracted favorably.

Referring again to FIG. 4, the concentration measurement apparatus 1 of the present embodiment performs the following operation. That is, the CPU 14 calculates the correlation coefficient of the temporal relative change amount of the oxygenated hemoglobin concentration ($\Delta O_2Hb$) and the temporal relative change amount of the deoxygenated hemoglobin concentration ($\Delta HHb$) that have been calculated by the method described above. Further, the CPU 14 calculates the polarity (positive or negative) of the slope of the regression line in the scatter diagram of the temporal relative change amount of the oxygenated hemoglobin concentration ($\Delta O_2Hb$) and the temporal relative change amount of the deoxygenated hemoglobin concentration ($\Delta HHb$) (calculation step, S15). Thereafter, the time series data indicating the temporal relative change amounts ($\Delta cHb$, $\Delta O_2Hb$, $\Delta HHb$), the correlation coefficient, and the polarity of the slope of the regression line are displayed together on the display section 15 (display step, S16). With the concentration measurement apparatus 1 and the concentration measurement method according to the present embodiment, the above-described steps S11 to S16 are repeated.

The object of calculating and the method of calculating the correlation coefficient of the temporal relative change amount of the oxygenated hemoglobin concentration ($\Delta O_2Hb$) and the temporal relative change amount of the deoxygenated hemoglobin concentration ($\Delta HHb$) and the polarity of the slope of the regression line in the scatter diagram of these amounts shall now be described in detail.

(a) in FIG. 9 to (a) in FIG. 13 are graphs of the measured values of the time series data of the temporal relative change amounts ($\Delta O_2Hb$, $\Delta HHb$). In each of (a) in FIG. 9 to (a) in FIG. 13, a graph G61 indicates the time series data of the temporal relative change amount of the oxygenated hemoglobin concentration ($\Delta O_2Hb$), and a graph G62 indicates the time series data of the temporal relative change amount of the deoxygenated hemoglobin concentration ($\Delta HHb$). Further, in each of (a) in FIG. 9 to (a) in FIG. 13, the horizontal axis represents the time (units: seconds), and the vertical axis represents the amplitude of the temporal relative change amount (arbitrary units). The phase shifts (phase differences) between the temporal relative change amounts ($\Delta O_2Hb$, $\Delta HHb$) in (a) in FIG. 9 to (a) in FIG. 13 are 0°, 45°, 90°, 135°, and 180°, respectively.

Further, (b) in FIG. 9 to (b) in FIG. 13 are scatter diagrams of the temporal relative change amount of the oxygenated hemoglobin concentration ($\Delta O_2Hb$) and the temporal relative change amount of the deoxygenated hemoglobin concentration ($\Delta HHb$), respectively corresponding to (a) in FIG. 9 to (a) in FIG. 13. In each of (b) in FIG. 9 to (b) in FIG. 13, the vertical axis represents the temporal relative change amount of the oxygenated hemoglobin concentration ($\Delta O_2Hb$, arbitrary units), and the horizontal axis represents the temporal relative change amount of the deoxygenated hemoglobin concentration ($\Delta HHb$, arbitrary units). Further, a line B drawn in each of (b) in FIG. 9 to (b) in FIG. 13 represents the regression line in the scatter diagram. In the scatter diagram of each of (b) in FIG. 9 to (b) in FIG. 13 are plotted 100 points resulting from measurement of the temporal relative change amounts ($\Delta O_2Hb$, $\Delta HHb$) for 5 seconds at a sampling rate of 20 times/second. Here, time series data of at least one cycle are sufficient for determining the correlation coefficient $R^2$ and the polarity of the slope of the regression line B to be described below.

Referring to FIG. 9, when the phase shift (phase difference) is 0°, the correlation coefficient $R^2$ takes on a high numerical value of approximately 0.89 and the polarity of the slope (approximately 1.56) of the regression line B is positive. Also, referring to FIG. 10, when the phase shift (phase difference) is 45°, the correlation coefficient $R^2$ takes on a comparatively low numerical value of approximately 0.33 and the polarity of the slope (approximately 0.96) of the regression line B is positive. Further, referring to FIG. 11, when the phase shift (phase difference) is 90°, the correlation coefficient $R^2$ is substantially zero and the value of the slope of the regression line B is also substantially zero. As these results show, when the phase shift (phase difference) is in a range of 0° to 90°, the polarity of the slope of the regression line is positive and the value of the correlation coefficient decreases with an increase in the phase shift.

Further, referring to FIG. 12, when the phase shift (phase difference) is 135°, the correlation coefficient $R^2$ takes on a comparatively low numerical value of approximately 0.29 and the polarity of the slope (approximately −0.89) of the regression line B is negative. Also, referring to FIG. 13, when the phase shift (phase difference) is 180°, the correlation coefficient $R^2$ takes on a high numerical value of approximately 0.89 and the polarity of the slope (approximately −1.56) of the regression line B is negative.

Figure 14:
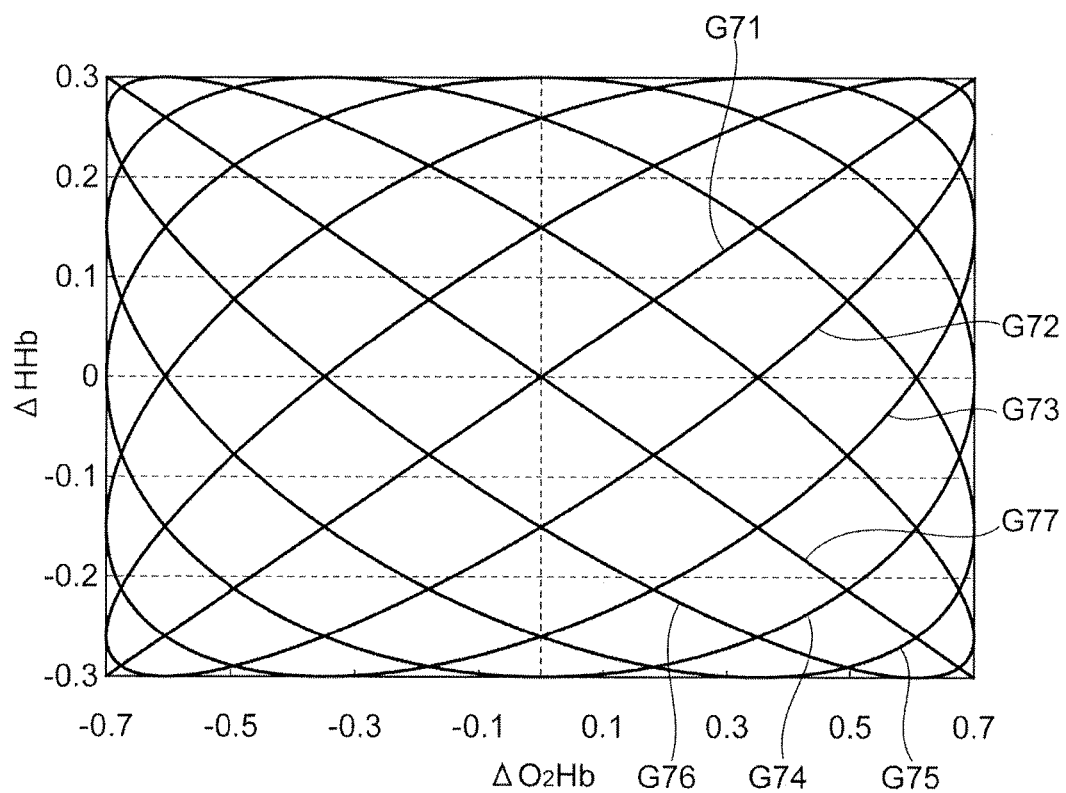
FIG. 14 is a graph of Lissajous figures of the temporal relative change amounts ($\Delta O_2 Hb$, $\Delta HHb$) obtained by changing the phase shift (phase difference) at 30° increments from 0° to 180°.

Thus, the correlation coefficient and the polarity of the slope of the regression line accurately express the phase shift between the temporal relative change amount of the oxygenated hemoglobin concentration ($\Delta O_2Hb$) and the temporal relative change amount of the deoxygenated hemoglobin concentration ($\Delta HHb$). FIG. 14 is a graph of Lissaious figures of the temporal relative change amounts ($\Delta O_2Hb$, $\Delta HHb$) obtained by changing the phase shift (phase difference) at 30° increments from 0° to 180°. In FIG. 14, graphs G71 to G77 indicate cases where the phase shift is 0°, 30°, 60°, 90°, 120°, 150°, and 180°, respectively. The ellipse swells and the correlation coefficient $R^2$ decreases as the phase shift increases from 0°, and when the phase shift exceeds 90°, the correlation coefficient $R^2$ increases again and a state similar to that at 0° is reached at 180° (reverse phase). On the other hand, the polarity of the slope of the regression line (the major axis of the ellipse) is positive when the phase shift is less than 90° and changes to being negative when 90° is exceeded.

The above results indicate that by referring to the polarity of the slope of the regression line B and the magnitude of the correlation coefficient $R^2$ together, the above-described phase shift can be made known accurately to enable accurate evaluation of the accuracy of calculation of the hemoglobin concentration and the oxygen saturation and the possibility of reverse direction blood transmission from the vena cava to the head.

Here, in a scatter diagram having x and y as variables, the slope k of the regression line and correlation coefficient $R^2$ can be determined respectively by the following formulas (9) and (10).

[Formula 9]
$$k = \frac{Sxy}{Sx} \tag{9}$$

[Formula 10]
$$R^2 = \frac{Sxy^2}{Sx \cdot Sy} \tag{10}$$

In the above, Sx is the variance of x, Sy is the variance of y, and Sxy is the covariance of x and y. The variances Sx and Sy and the covariance Sxy are determined respectively by the following formulas (11) to (13). Here, $x_0$ and $y_0$ are the average values of x and y, respectively. Also, n is the number of samples.

[Formula 11]
$$Sx = \frac{1}{n}\sum_{i=1}^{n}(x_i - x_0)^2 \tag{11}$$

-continued

[Formula 12]
$$Sy = \frac{1}{n}\sum_{i=1}^{n}(y_i - y_0)^2 \quad (12)$$

[Formula 13]
$$Sxy = \frac{1}{n}\sum_{i=1}^{n}(x_i - x_0)(y_i - y_0) \quad (13)$$

Here, in the concentration measurement apparatus 1, the variances Sx and Sy and the covariance Sxy may be determined by the following method to perform the calculation process rapidly. That is, the variances Sx and Sy and the covariance Sxy can also be favorably determined respectively by the following formulas (14) to (16).

[Formula 14]
$$Sx = \sum_{i=1}^{n}(x_i^2 - nx_0^2) \quad (14)$$

[Formula 15]
$$Sy = \sum_{i=1}^{n}(y_i^2 - ny_0^2) \quad (15)$$

[Formula 16]
$$Sxy = \sum_{i=1}^{n}(x_i y_i - nx_0 y_0) \quad (16)$$

Thus, the variances Sx and Sy, the covariance Sxy, and the average values $x_0$ and $y_0$ may be determined, for example, for the time series data of the temporal relative change amount of the oxygenated hemoglobin concentration ($\Delta O_2Hb$) obtained in a given time (for example, 5 seconds) as $x_1$ to $x_n$ and the time series data of the temporal relative change amount of the deoxygenated hemoglobin concentration ($\Delta HHb$) as $y_1$ to $y_n$. Further, these are then substituted into the above-described formulas (9) and (10) to determine the slope k of the regression line and the correlation coefficient $R^2$.

Further, to determine the oxygen saturation, the slope k may be determined by the above-described formula (9) for the time series data of the temporal relative change amount of the total hemoglobin concentration ($\Delta cHb$) as $x_1$ to $x_n$ and the time series data of the temporal relative change amount of the oxygenated hemoglobin concentration ($\Delta O_2Hb$) as $y_1$ to $y_n$. The oxygen saturation SO2 is calculated as SO2=k× 100(%).

The effects of the concentration measurement apparatus 1 and the concentration measurement method according to the present embodiment having the above configuration shall now be described.

As described above, to improve the reliability of measurement and calculation concerning the oxygenated hemoglobin concentration and deoxygenated hemoglobin concentration using near-infrared light, it is important for these hemoglobin concentrations to vary in the same phase mutually and in synchronization with the timing of chest compression. However, these do not necessarily vary in the same phase in the case of chest compression of a cardiopulmonary arrest person. This is because, in chest compression, blood flow is caused by pressing of the entire arrested heart, and therefore, blood transmission in the reverse direction from the vena cava occurs readily, and becomes a cause of a shift between the phase of the oxygenated hemoglobin concentration and the phase of the deoxygenated hemoglobin concentration in the head.

Thus, the accuracy of measurement calculation concerning the oxygenated hemoglobin concentration and the deoxygenated hemoglobin concentration using near-infrared light is compromised, and it is difficult to obtain correct numerical values for the amplitude of the total hemoglobin concentration and the oxygen saturation that are calculated based on these. Also, blood transmission in the reverse direction from the vena cava to the brain is, in itself, unfavorable.

With the concentration measurement apparatus 1 and the concentration measurement method according to the present embodiment, the temporal relative change amounts of the oxygenated hemoglobin concentration and the deoxygenated hemoglobin concentration ($\Delta O_2Hb$, $\Delta HHb$) are determined, and further, the correlation coefficient $R^2$ of the temporal relative change amount of the oxygenated hemoglobin concentration ($\Delta O_2Hb$) and the temporal relative change amount of the deoxygenated hemoglobin concentration ($\Delta HHb$), and the polarity (positive or negative) of the slope k of the regression line B in the scatter diagram of these relative change amounts ($\Delta O_2Hb$, $\Delta HHb$) are determined. As described above, the correlation coefficient $R^2$ and the polarity of the slope k of the regression line B accurately express the phase shift between the oxygenated hemoglobin concentration and the deoxygenated hemoglobin concentration.

The phase shift between the oxygenated hemoglobin concentration and the deoxygenated hemoglobin concentration can thus be made known accurately by referring to the polarity of the slope k of the regression line B and the magnitude of the correlation coefficient $R^2$ together. That is, with the concentration measurement apparatus 1 and the concentration measurement method according to the present embodiment, the CPU 14 determines the polarity of the slope k of the regression line B and the magnitude of the correlation coefficient $R^2$ to enable the accuracy of calculation of the amplitude of the total hemoglobin concentration and the oxygen saturation and the possibility of reverse direction blood transmission from the vena cava to the head to be evaluated easily based on the phase shift between the oxygenated hemoglobin concentration and the deoxygenated hemoglobin concentration.

Here, (a) in FIG. 15 is a graph of time series data resulting from mixing noise in the temporal relative change amounts ($\Delta O_2Hb$, $\Delta HHb$) shown in (a) in FIG. 9. A graph G81 indicates the time series data of the temporal relative change amount of the oxygenated hemoglobin concentration ($\Delta O_2Hb$), and a graph G82 indicates the time series data of the temporal relative change amount of the deoxygenated hemoglobin concentration ($\Delta HHb$). Further, (b) in FIG. 15 is a scatter diagram of the temporal relative change amounts ($\Delta O_2Hb$, $\Delta HHb$) corresponding to (a) in FIG. 15. A straight line B drawn in (b) in FIG. 15 represents the regression line. Referring to FIG. 15, even when the phase shift (phase difference) is 0°, the correlation coefficient $R^2$ indicates a low numerical value of approximately 0.22 due to the mixing of noise. The concentration measurement apparatus 1 and the concentration measurement method according to the present embodiment thus enables the evaluation of the reliability of calculations in the case where noise is mixed in the temporal relative change amounts of the oxygenated hemoglobin concentration and the deoxygenated hemoglobin concentration ($\Delta O_2Hb$, $\Delta HHb$).

Also, based on the temporal relative change amounts ($\Delta O_2Hb$, $\Delta HHb$), the CPU 14 may further determine the temporal relative change amount of the total hemoglobin concentration ($\Delta cHb$), and the display section 15 may display this temporal relative change amount ($\Delta cHb$) together with the correlation coefficient $R^2$ and the polarity of the slope k of the regression line B. A chest compression performer, etc., can thereby easily check the accuracy of calculation of the temporal relative change amount of the total hemoglobin concentration ($\Delta cHb$) based on the phase shift between the oxygenated hemoglobin concentration and the deoxygenated hemoglobin concentration. In this case, the display section 15 preferably displays the correlation coefficient $R^2$, for example, as a numeral or in a graph.

Also, based on the temporal relative change amounts ($\Delta O_2Hb$, $\Delta HHb$), the CPU 14 may further determine the oxygen saturation SO2, and the display section 15 may display the oxygen saturation SO2 together with the correlation coefficient $R^2$ and the polarity of the slope k of the regression line B. A chest compression performer, etc., can thereby easily check the accuracy of calculation of the oxygen saturation SO2 based on the phase shift between the oxygenated hemoglobin concentration and the deoxygenated hemoglobin concentration. The display section 15 preferably displays the correlation coefficient $R^2$, for example, as a numeral or in a graph, in this case as well.

The concentration measurement apparatus and the concentration measurement method according to the present invention is not restricted to the embodiment described above, and various modifications are possible. For example, although with the concentration measurement apparatus 1 and the concentration measurement method according to the above-described embodiment, the respective relative change amounts ($\Delta cHb$, $\Delta O_2Hb$, $\Delta HHb$) of the total hemoglobin concentration, oxygenated hemoglobin concentration, and deoxygenated hemoglobin concentration are determined, with the concentration measurement apparatus and concentration measurement method according to the present invention, material for making an objective judgment of whether or not chest compression is being performed appropriately can be indicated by determining at least one of the respective relative change amounts ($\Delta cHb$, $\Delta O_2Hb$) of the total hemoglobin concentration and oxygenated hemoglobin concentration.

Also, the filtering process in the concentration measurement apparatus and concentration measurement method according to the present invention is not restricted to those given as examples in the embodiment, and any filtering process capable of removing frequency components less than a predetermined frequency from the relative change amounts ($\Delta cHb$, $\Delta O_2Hb$) may be used favorably in the present invention.

Also with the present invention, the hemoglobin oxygen saturation (TOI), determined by near-infrared spectral analysis in a manner similar to the respective relative change amounts ($\Delta cHb$, $\Delta O_2Hb$, $\Delta HHb$) of the total hemoglobin concentration, oxygenated hemoglobin concentration, and deoxygenated hemoglobin concentration, may be displayed in a graph or as a numerical value together with the relative change amounts on the display section. Improvement of the brain oxygen state by the chest compression can thereby be checked to maintain the motivation of the chest compression performer. The TOI may be an average value for a predetermined duration (for example, 5 seconds).

Here, with the concentration measurement apparatus and the concentration measurement method described above, the accuracy of calculation, etc., based on the phase shift between the oxygenated hemoglobin concentration and the deoxygenated hemoglobin concentration is evaluated by the correlation coefficient and the polarity of the slope of the regression line. However, it is also possible to evaluate the accuracy of calculation, etc., by calculating the phase shift itself between the oxygenated hemoglobin concentration and the deoxygenated hemoglobin concentration. The phase shift between the oxygenated hemoglobin concentration and the deoxygenated hemoglobin concentration is calculated favorably, for example, by either of the following first and second methods.

(First Method)

First, amplitudes $A_{\Delta O2Hb}$, $A_{\Delta HHb}$, and $A_{\Delta cHb}$ of the respective relative change amounts of the oxygenated hemoglobin concentration, deoxygenated hemoglobin concentration, and total hemoglobin concentration ($\Delta O_2Hb$, $\Delta HHb$, $\Delta cHb$) are determined. Here, if the phase difference between the oxygenated hemoglobin concentration and deoxygenated hemoglobin concentration is $\theta$.

$$A_{\Delta cHb}^2 = A_{\Delta O2Hb}^2 + A_{\Delta HHb}^2 + 2A_{\Delta O2Hb}A_{\Delta HHb}\cos\theta$$

and therefore, the phase difference is calculated by the following calculation formula.

$$\theta = \cos^{-1}\{(A_{\Delta cHb} - A_{\Delta O2Hb} - A_{\Delta HHb})/2A_{\Delta O2Hb}A_{\Delta HHb}\}$$

Therefore, for example, the phase difference $\theta$ is determined from the average amplitudes of the respective relative change amounts ($\Delta O_2Hb$, $\Delta HHb$, $\Delta cHb$) in the past 5 seconds and this phase difference $\theta$ is renewed every 1 second, for example, and displayed on the display section. Also, the ratio $A_{\Delta cHb}/(A_{\Delta O2Hb}+A_{\Delta HHb})$ of $A_{\Delta cHb}$ and $(A_{\Delta O2Hb}+A_{\Delta HHb})$ may be displayed as a parameter that serves as an approximate reference for the phase difference $\theta$. The value of this parameter is 1 when $\Delta O_2Hb$ and $\Delta HHb$ are in the same phase mutually, and decreases as the phase difference increases.

(Second Method)

First, a cross-correlation function $z(\tau)$ of the oxygenated hemoglobin concentration $O_2Hb(t)$ and the deoxygenated hemoglobin concentration $HHb(t)$ as indicated by formula (17) is calculated for a single noted data analysis range T (of, for example, 5 seconds) (t=0 to T). In this process, $\tau$ is varied at increments of a measurement cycle (for example, 1/20 seconds) from 0 to calculate $Z(\tau)$ over at least a variation cycle (t0).

[Formula 17]

$$Z(\tau) = \int_0^T O_2Hb(t) \cdot HHb(t-\tau)dt (\tau = 0 \sim T) \quad (17)$$

Next, the time ($\tau$=T0) at which the cross-correlation function $z(\tau)$ peaks is determined. Then, the phase difference $\theta$ is calculated using the relational expression $\theta=360\times(T0/t0)$. For example, the time T0 and the phase difference $\theta$ is determined using the oxygenated hemoglobin concentration $O_2Hb(t)$ and the deoxygenated hemoglobin concentration $HHb(t)$ for the past 5 seconds, and these are renewed every 1 second, for example, and displayed on the display section.

For displaying the phase difference $\theta$ on the display section, there are, for example, a method of displaying the actual waveform of the oxygenated hemoglobin concentration $O_2Hb(t)$ and the deoxygenated hemoglobin concentration HHb(t), a method of displaying the phase difference θ as a numeral (0°, 20°, etc.), etc. Further, a cautionary display is preferably performed together with the display of the amplitude value of the total hemoglobin concentration and the oxygen saturation value, when the phase difference θ exceeds a predetermined value. For example, when the phase difference θ indicates a shift of no less than 30° (COS θ<0.86), the numeral is blinked in yellow, and when the phase difference θ indicates a shift of no less than 60° (COS θ<0.50), the numeral is blinked in red.

Also, in the concentration measurement apparatus and the concentration measurement method of measuring the temporal relative change amounts of the oxygenated hemoglobin concentration and the deoxygenated hemoglobin concentration in the head that vary due to repetition of chest compression, the calculation section preferably includes filtering process means (filtering process step) that removes frequency components less than a predetermined frequency from frequency components contained in the relative change amounts of the first temporal relative change amount of the oxygenated hemoglobin concentration and the second temporal relative change amount of the deoxygenated hemoglobin concentration. Information related to changes in concentration due to the chest compression can thereby be extracted favorably.

The concentration measurement apparatus according to the embodiment is a concentration measurement apparatus for measuring temporal relative change amounts of oxygenated hemoglobin concentration and deoxygenated hemoglobin concentration, that vary due to repetition of chest compression, in a head, and has a configuration including a light incidence section irradiating the head with measurement light, a light detection section detecting the measurement light that has propagated through the interior of the head and generating a detection signal in accordance with the intensity of the detected measurement light, and a calculation section determining, based on the detection signal, a correlation coefficient of a first temporal relative change amount of the oxygenated hemoglobin concentration and a second temporal relative change amount of the deoxygenated hemoglobin concentration and the polarity of the slope of a regression line of the first relative change amount and the second relative change amount.

Also, the concentration measurement method according to the embodiment is a concentration measurement method of measuring temporal relative change amounts of oxygenated hemoglobin concentration and deoxygenated hemoglobin concentration, that vary due to repetition of chest compression, in a head, and has a configuration including a light incidence step of irradiating the head with measurement light, a light detection step of detecting the measurement light that has propagated through the interior of the head and generating a detection signal in accordance with the intensity of the detected measurement light, and a calculation step of determining, based on the detection signal, a correlation coefficient of a first temporal relative change amount of the oxygenated hemoglobin concentration and a second temporal relative change amount of the deoxygenated hemoglobin concentration and the polarity of the slope of a regression line of the first relative change amount and the second relative change amount.

Also, the above-described concentration measurement apparatus and the concentration measurement method may be of configurations, in which the calculation section further determines a temporal relative change amount of the total hemoglobin concentration based on the first and second relative change amounts, and which further include a display section displaying the temporal relative change amount of the total hemoglobin concentration together with the correlation coefficient and the polarity of the slope of the regression line. A chest compression performer, etc., can thereby easily check the accuracy of the temporal relative change amount of the total hemoglobin concentration based on the phase shift between the oxygenated hemoglobin concentration and the deoxygenated hemoglobin concentration. In this case, the display section may display the correlation coefficient by at least one of a numeral and a graph.

Also, the above-described concentration measurement apparatus and the concentration measurement method may be of configurations, in which the calculation section further determines an oxygen saturation based on the first and second relative change amounts, and which further include a display section displaying the oxygen saturation together with the correlation coefficient and the polarity of the slope of the regression line. A chest compression performer, etc., can thereby easily check the accuracy of the oxygen saturation based on the phase shift between the oxygenated hemoglobin concentration and the deoxygenated hemoglobin concentration. In this case, the display section may display the correlation coefficient by at least one of a numeral and a graph.

INDUSTRIAL APPLICABILITY

The present invention can be used as a concentration measurement apparatus and a concentration measurement method that enable evaluation of the accuracy of calculation and the possibility of reverse direction blood transmission from the vena cava to the head based on a phase shift between an oxygenated hemoglobin concentration and a deoxygenated hemoglobin concentration.

REFERENCE SIGNS LIST

1—concentration measurement apparatus, 10—main unit section, 11—light emitting section, 12—sample hold circuit, 13—converter circuit, 14—calculation section, 15—display section, 18—data bus, 20—probe, 21—light incidence section, 22—light detection section, 23—holder, 24—optical fiber, 25—prism, 26—photodetection element, 27—pre-amplifier section, 28—cable, 51—head, B—regression line

The invention claimed is:

1. An apparatus for measuring temporal relative change amounts of oxygenated hemoglobin concentration and deoxygenated hemoglobin concentration, that vary due to repetition of chest compression, in a head, comprising:
 a light source configured to output measurement light;
 a light detector configured to detect the measurement light that has propagated through the interior of the head and generate a detection signal in accordance with the intensity of the detected measurement light; and
 a processor that is electrically coupled to the light detector and programmed to:
 determine, based on the detection signal, a temporal relative change amount of the oxygenated hemoglobin concentration and a temporal relative change amount of the deoxygenated hemoglobin concentration that vary due to repetition of chest compression,
 determine a phase shift between the temporal relative change amount of the oxygenated hemoglobin concentration and the temporal relative change amount of the deoxygenated hemoglobin concentration, and
 evaluate the chest compression based on the phase shift.

2. The apparatus according to claim 1, wherein the processor is programmed to evaluate occurrence of reverse direction blood transmission from the vena cava to the head in the chest compression based on the phase shift.

3. The apparatus according to claim 1, wherein the processor is programmed to apply a filtering process to the temporal relative change amounts of the oxygenated hemoglobin concentration and the deoxygenated hemoglobin concentration to remove frequency components less than a predetermined frequency for extracting temporal variation components of the oxygenated hemoglobin concentration and the deoxygenated hemoglobin concentration due to the repetition of the chest compression.

4. The apparatus according to claim 1, wherein the measurement light is near-infrared light.

5. The apparatus according to claim 1, further comprising a display configured to display a measurement result.

6. A method for measuring temporal relative change amounts of oxygenated hemoglobin concentration and deoxygenated hemoglobin concentration, that vary due to repetition of chest compression, in a head, comprising:
  irradiating the head with measurement light;
  detecting the measurement light that has propagated through the interior of the head and generating a detection signal in accordance with the intensity of the detected measurement light;
  determining, based on the detection signal, a temporal relative change amount of the oxygenated hemoglobin concentration and a temporal relative change amount of the deoxygenated hemoglobin concentration that vary due to repetition of chest compression;
  determining a phase shift between the temporal relative change amount of the oxygenated hemoglobin concentration and the temporal relative change amount of the deoxygenated hemoglobin concentration; and
  evaluating the chest compression based on the phase shift.

7. The method according to claim 6, wherein the evaluating evaluates occurrence of reverse direction blood transmission from the vena cava to the head in the chest compression based on the phase shift.

8. The method according to claim 6, further comprising applying a filtering process to the temporal relative change amounts of the oxygenated hemoglobin concentration and the deoxygenated hemoglobin concentration to remove frequency components less than a predetermined frequency for extracting temporal variation components of the oxygenated hemoglobin concentration and the deoxygenated hemoglobin concentration due to the repetition of the chest compression.

9. The method according to claim 6, wherein the measurement light is near-infrared light.

10. The method according to claim 6, further comprising displaying a measurement result.

* * * * *